US007511052B2

(12) United States Patent
Semko et al.

(10) Patent No.: US 7,511,052 B2
(45) Date of Patent: Mar. 31, 2009

(54) PYRIMIDINYL AMIDE COMPOUNDS WHICH INHIBIT LEUKOCYTE ADHESION MEDIATED BY VLA-4

(75) Inventors: Christopher Michael Semko, Fremont, CA (US); Ying-zi Xu, Palo Alto, CA (US); Frank Stappenbeck, Seattle, WA (US); Jenifer Lea Smith, South San Francisco, CA (US); Kassandra Inez Rossiter, San Jose, CA (US); Juri Y. Fukuda, Oakland, CA (US); Andrei W. Konradi, Burlingame, CA (US)

(73) Assignees: Elan Pharmaceuticals, Inc., South San Francisco, CA (US); Wyeth, Madison, NJ (US)

( * ) Notice: Subject to any disclaimer, the term of this patent is extended or adjusted under 35 U.S.C. 154(b) by 0 days.

(21) Appl. No.: 11/529,815

(22) Filed: Sep. 28, 2006

(65) Prior Publication Data

US 2007/0142416 A1 Jun. 21, 2007

Related U.S. Application Data

(60) Provisional application No. 60/722,358, filed on Sep. 29, 2005.

(51) Int. Cl.
*C07D 239/50* (2006.01)
*C07D 401/12* (2006.01)
*C07D 401/14* (2006.01)
*A61K 31/505* (2006.01)
*A61K 31/506* (2006.01)
*A61P 29/00* (2006.01)
*A61P 19/02* (2006.01)

(52) U.S. Cl. .................. 514/275; 544/323; 544/324; 544/325

(58) Field of Classification Search ............. 544/323, 544/324, 325; 514/275
See application file for complete search history.

(56) References Cited

U.S. PATENT DOCUMENTS

| 4,235,871 | A | 11/1980 | Papahadjopoulos et al. |
| 4,501,728 | A | 2/1985 | Geho et al. |
| 4,837,028 | A | 6/1989 | Allen et al. |
| 5,011,472 | A | 4/1991 | Aebischer et al. |
| 5,023,252 | A | 6/1991 | Hseih et al. |
| 6,436,904 | B1 | 8/2002 | Ashwell et al. |
| 6,492,372 | B1 | 12/2002 | Ashwell et al. |
| 2006/0013799 | A1 | 1/2006 | Konradi et al. |

FOREIGN PATENT DOCUMENTS

| EP | 0330506 | 8/1989 |
| WO | WO 98/53817 | 12/1998 |
| WO | WO99/06390 | 2/1999 |
| WO | WO 00/43372 | 7/2000 |
| WO | WO 03/099809 | 12/2003 |
| WO | WO 2005/111020 | 11/2005 |

OTHER PUBLICATIONS

Wolft Manfred E. "Burger's Medicinal Chemistry, 5ed, Part 1", John Wiley & Sons, 1995, pp. 975-977.*
Banker, G.S. et al, "Modern Pharmaceutices, 3ed.", Marcel Dekker, New York. 1996, pp. 451 and 596.*
Tarkowski et al. Int. Arch. Allergy Immunol. 121(1) 25-33, 2000.*
Grayson et al., J. Exp. Med., 188(11), 2187-2191, 1998.*
Tiley et al., Drugs of the Future, 26(10), 985-998, 2001.*
Abraham et al. "$\alpha_4$-Integrins Mediate Antigen-induced Late Bronchial Responses and Prolonged Airway Hyperresponsiveness in Sheep" *J. Clin. Invest.* 93:776-787 (1994).
Chen et al. "Mediation of Sperm-Egg Fusion: Evidence that Mouse Egg $\alpha_6\beta_1$ Integrin is the Receptor for Sperm Fertilin$\beta$" *Chem Biol.* 6:1-10 (1999).
Cybulsky et al. "Endothelial Expression of a Mononuclear Leukocyte Adhesion Molecule During Atherogenesis" *Science* 251:788-791 (1991).
Elewaut et al. "Distinctive Activated Cellular Subsets in Colon from Patients with Crohn's Disease and Ulcerative Colitis" *Scand. J. Gastroenterol* 33:743-748 (1998).
Elices et al. "VCAM-1 on Activated Endothelium Interacts with the Leukocyte Integrin VLA-4 at a Site Distance from the VLA-4/Fibronectin Binding Site" *Cell* 60:577-584 (1990).
Elices et al. "Expression and Functional Significance of Alternatively Spliced CS1 Fibronectin in Rheumatoid Arthritis Microvasculature" *J. Clin. Invest.* 93:405-416 (1994).
Freedman et al. "Adhesion of Follicular Lymphoma Cells to Lymphoid germinal Centers—A Potential Mechanism of Tumor Cell Homing Following Autologous Transplantation" *Leuk. And Lymphoma* 13:47-52(1994).
Georczynski et al. "Manipulation of Skin Graft Rejection in Alloimmune Mice by Anti-VCAM-1:VLA-4 but not Anti-ICAM-1:LFA-1 Monoclonal Antibodies" *Trans. Immunl* 3:55-61 (1995).
Georczynski et al. "Altered Patters of Migration of Cytokine-Producing T Lymphocytes in Skin-Grafted Naïve or Immune Mice Following in Vivo Administration of Anti-VCAM-1 or ICAM-1" *Immunology* 87:573-580 (1996).
Grayson et al. "$\alpha$d$\beta$2 Integrin Is Expressed on Human Eosinophils and Functions as an Alternative Ligand for Vascular Cell Adhesion Molecule 1 (VCAM-1)" *J. Exp. Med.* 188(11) 2187-2191 (1998).
Hamann et al. "Role of $\alpha_4$-Integrins in Lymphocyte Homing to Muscosal Tissues in Vivo" *Immunology*, 152:3282-3293 (1994).
Hopewell et al. "Models fo CNS Radiation Damage During Space Flight" *Adv. Space. Res.* 14:433-442 (1994).

(Continued)

*Primary Examiner*—Venkataraman Balasubramanian
(74) *Attorney, Agent, or Firm*—Foley & Lardner LLP

(57) ABSTRACT

Disclosed are compounds which bind VLA-4. Certain of these compounds also inhibit leukocyte adhesion and, in particular, leukocyte adhesion mediated by VLA-4. Such compounds are useful in the treatment of inflammatory diseases in a human or animal subject such as asthma, Alzheimer's disease, atherosclerosis, AIDS dementia, diabetes, inflammatory bowel disease, rheumatoid arthritis, tissue transplantation, tumor metastasis and myocardial ischemia. The compounds can also be administered for the treatment of inflammatory brain diseases such as multiple sclerosis.

30 Claims, No Drawings

OTHER PUBLICATIONS

Kawaguchi et al. "VLA-4 Molecules on Tumor Cells Initiate and Adhesive Interaction with VCAM-1 Molecules on Endothelial Cell Surface" *Japanese J. Cancer Res.* 83:1304-1316 (1992).

Kroneld et al. "Expression of the Mucosal Lymphocyte Integrin $\alpha^E\beta_7$ and its Ligand E-cadherin in Salivary Glands of Patients with Sjögren's Syndrome" *Scand. J. Rheumatol* 27(3):215-218 (1998).

Kung et al. "Involvement of IL-5 in a Murine Model of Allergic Pulmonary Inflammation: Prophylactic and Therapeutic Effect of an Anti-IL-5 Antibody" *Am. J. Respir. Cell. Mol. Biol.* 13:360-365 (1995).

Lauri et al. "Decreased Adhesion to Endothelial Cells and Matrix Proteins of H-2K Gene Transfected Tumour Cells" *British J. Cancer*, 68:862-867 (1993).

Li et al. "An Atherogenic Diet Rapidly Induces VCAM-1, a Cytokine-Regulatable Mononuclear Leukocyte Adhesion Molecule, in Rabbit Aortic Endothelium" *Arterioscler. Thromb* 13:197-204 (1993).

Mulligan et al. "Role of $\beta_1$, $\beta_2$ Integrins and ICAM-1 in Lung Injury after Deposition of IgG and Iga Immune Complexes" *J. Immunology* 150:2407-2417 (1993).

Okarhara et al. "Involvement of Very Late Activation Antigen 4 (VLA-4) and Vascular Cell Adhesion Molecule 1 (VCAM-1) in Tumor Necrosis Factor α Enhancement of Experimental Metastasis" *Can. Res.* 54:3233-3236 (1994).

Orosz et al. "Promotion of Experimental Liver Metastasis by Tumor Necrosis Factor" *Int. J. Cancer*60:867-871 (1995).

Osborne, Laurelee, "Leukocyte Adhesion to Endothelium in Inflammation" *Cell* 62:3-6 (1990).

Paavonen et al. "In Vivo Evidence of the Role of $\alpha 4\beta 1$-VCAM-1 Interaction in Sarcoma, but not in Carcinoma Extravasation" *Int. J. Can.* 58:298-302 (1994).

Palmer et al. "Sequence and Tissue Distribution of the Integrin $\alpha 9$ Subunit, a Novel Partner of $\beta 1$ that is Widely Distributed in Epithelia and Muscle" *J. Cell Biol.* 123(5) 1289-1297 (1993).

Pang et al. "UP-Regulation of $\alpha E\beta 7$, A Novel Integrin Adhesion Molecule, on T Cells from Systemic Lupis Erythematosus Patients with Specific Epithelial Involvement" *Arthritis & Reumatism* 41(8):1456-1463 (1998).

Paul et al. "Monoclonal Antibodies Against LFA-1 and VLA-4 Inhibit Graft Vasculitis in Rat Cardiac Allografts" *Transpl. Proceed.* 25:813-814 (1993).

Paul et al. "Anti-Integrin (LFA-1, VLA-4, and Mac-1) Antibody Treatment and Acute Cardiac Graft Rejection in the Rat" *Transpl. Int.* 9:420-425 (1996).

Steinbach et al. "Expression of Cell Adhesion Molecules in an Established and Characterized New Human Renal Cell Cancer Line, CCF-RC7" *Urol. Res.* 23:175-183 (1995).

Trollmo et al. "Expression of the Mucosal Lymphocyte Integrin $\alpha^E\beta_7$ and its Ligand E-Cadherin in the Synovium of patients with Rheumatoid Arthritis" *Scand. J. Immunol.* 44:293-298 (1996).

Yednock et al. "$\alpha_4\beta_1$Integrin-Dependent Cell Adhesion Is Regulated by a Low Affinity Receptor Pool That Is Conformationally Responsive to Ligand" *J. Biol. Chem.*, 270(48):28740-28750 (1995).

Yokosaki et al. "The Integrin $\alpha 9\beta 1$ Mediates Cell Attachment to a Non-RGD Site in the Third Fibronection Type III Repeat of Tenascin" *J. Biol. Chem.* 269:26691-26696 (1994).

U.S. Appl. No. 11/541,205, filed Sep. 28, 2006, Semko et al.

\* cited by examiner

PYRIMIDINYL AMIDE COMPOUNDS WHICH INHIBIT LEUKOCYTE ADHESION MEDIATED BY VLA-4

CROSS REFERENCES TO RELATED APPLICATIONS

This application claims the benefit under 35 U.S.C. § 119 (e) of U.S. Provisional Application No. 60/722,358, filed Sep. 29, 2005, which is hereby incorporated by reference in it entirety.

BACKGROUND OF THE INVENTION

Field of the Invention

This invention relates to compounds which inhibit leukocyte adhesion and, in particular, leukocyte adhesion mediated by α4 integrins, where the α4 integrin is preferably VLA-4. This invention also relates to pharmaceutical compositions comprising such compounds as well as methods for treating, e.g., inflammation, using either the compounds or the pharmaceutical compositions of this invention.

REFERENCES

The following publications are cited in this application as superscript numbers:

1 Hemler and Takada, European Patent Application Publication No. 330,506, published Aug. 30, 1989
2 Elices, et al., Cell, 60:577 584 (1990)
3 Springer, Nature, 346:425 434 (1990)
4 Osborn, Cell, 62:3 6 (1990)
5 Vedder, et al., Surgery, 106:509 (1989)
6 Pretolani, et al., J. Exp. Med., 180:795 (1994)
7 Abraham, et al., J. Clin. Invest., 93:776 (1994)
8 Mulligan, et al., J. Immunology, 150:2407 (1993)
9 Cybulsky, et al., Science, 251:788 (1991)
10 Li, et al., Arterioscler. Thromb., 13:197 (1993)
11 Sasseville, et al., Am. J. Path., 144:27 (1994)
12 Yang, et al., Proc. Nat. Acad. Science (USA), 90:10494 (1993)
13 Burkly, et al., Diabetes, 43:529 (1994)
14 Baron, et al., J. Clin. Invest., 93:1700 (1994)
15 Hamann, et al., J. Immunology, 152:3238 (1994)
16 Yednock, et al., Nature, 356:63 (1992)
17 Baron, et al., J. Exp. Med., 177:57 (1993)
18 van Dinther-Janssen, et al., J. Immunology, 147:4207 (1991)
19 van Dinther-Janssen, et al., Annals. Rheumatic Dis., 52:672 (1993)
20 Elices, et al., J. Clin. Invest., 93:405 (1994)
21 Postigo, et al., J. Clin. Invest., 89:1445 (1991)
22 Paul, et al., Transpl. Proceed., 25:813 (1993)
23 Okarhara, et al., Can. Res., 54:3233 (1994)
24 Paavonen, et al., Int. J. Can., 58:298 (1994)
25 Schadendorf, et al., J. Path., 170:429 (1993)
26 Bao, et al., Diff., 52:239 (1993)
27 Lauri, et al., British J. Cancer, 68:862 (1993)
28 Kawaguchi, et al., Japanese J. Cancer Res., 83:1304 (1992)
29 Konradi, et al., PCT/US00/01686, filed, Jan. 21, 2000

All of the above publications are herein incorporated by reference in their entirety to the same extent as if each individual publication was specifically and individually indicated to be incorporated by reference in its entirety.

STATE OF THE ART

VLA-4 (also referred to as α4β1 integrin and CD49d/CD29), first identified by Hemler and Takada,[1] is a member of the β1 integrin family of cell surface receptors, each of which comprises two subunits, an α chain and a β chain. VLA-4 contains an α4 chain and a β1 chain. There are at least nine β1 integrins, all sharing the same β1 chain and each having a distinct α chain. These nine receptors all bind a different complement of the various cell matrix molecules, such as fibronectin, laminin, and collagen. VLA-4, for example, binds to fibronectin. VLA-4 also binds non-matrix molecules that are expressed by endothelial and other cells. These non-matrix molecules include VCAM-1, which is expressed on cytokine-activated human umbilical vein endothelial cells in culture. Distinct epitopes of VLA-4 are responsible for the fibronectin and VCAM-1 binding activities and each activity has been shown to be inhibited independently.[2]

Intercellular adhesion mediated by VLA-4 and other cell surface receptors is associated with a number of inflammatory responses. At the site of an injury or other inflammatory stimulus, activated vascular endothelial cells express molecules that are adhesive for leukocytes. The mechanics of leukocyte adhesion to endothelial cells involves, in part, the recognition and binding of cell surface receptors on leukocytes to the corresponding cell surface molecules on endothelial cells. Once bound, the leukocytes migrate across the blood vessel wall to enter the injured site and release chemical mediators to combat infection. For reviews of adhesion receptors of the immune system, see, for example, Springer[3] and Osborn.[4]

Inflammatory brain disorders, such as experimental autoimmune encephalomyelitis (EAE), multiple sclerosis (MS) and meningitis, are examples of central nervous system disorders in which the endothelium/leukocyte adhesion mechanism results in destruction to otherwise healthy brain tissue. Large numbers of leukocytes migrate across the blood brain barrier (BBB) in subjects with these inflammatory diseases. The leukocytes release toxic mediators that cause extensive tissue damage resulting in impaired nerve conduction and paralysis.

In other organ systems, tissue damage also occurs via an adhesion mechanism resulting in migration or activation of leukocytes. For example, it has been shown that the initial insult following myocardial ischemia to heart tissue can be further complicated by leukocyte entry to the injured tissue causing still further insult (Vedder, et al.).[5] Other inflammatory or medical conditions mediated by an adhesion mechanism include, by way of example, asthma,[6-8] Alzheimer's disease, atherosclerosis,[9-10] AIDS dementia,[11] diabetes[12-14] (including acute juvenile onset diabetes), inflammatory bowel disease[15] (including ulcerative colitis and Crohn's disease), multiple sclerosis,[16-17] rheumatoid arthritis,[18-21] tissue transplantation,[22] tumor metastasis,[23-28] meningitis, encephalitis, stroke, and other cerebral traumas, nephritis, retinitis, atopic dermatitis, psoriasis, myocardial ischemia and acute leukocyte-mediated lung injury such as that which occurs in adult respiratory distress syndrome.

Substituted aminopyrimidines, as a class, have been disclosed as inhibiting binding of VLA-4 to VCAM-1 and, accordingly, exhibit anti-inflammatory properties.[29] While these compounds possess antagonist properties to such binding, enhanced bioavailability of these compounds would augment their efficacy.

SUMMARY OF THE INVENTION

This invention provides compounds, pharmaceutically acceptable salts thereof, compositions thereof, syntheses thereof, and methods for treating VLA-4 mediated diseases.

In one embodiment, the present invention provides compounds of formula I:

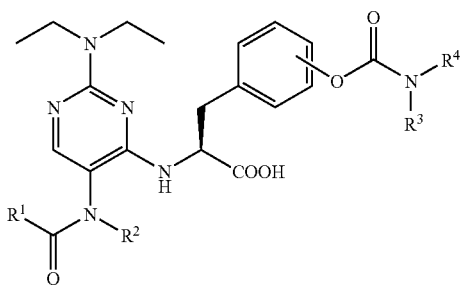

I wherein:

$R^1$ is selected from the group consisting of $C_1$ to $C_4$ alkyl, $C_1$ to $C_4$ haloalkyl, heteroaryl and —N($R^5$)($R^6$) where $R^5$ and $R^6$ are independently selected from the group consisting of hydrogen, $C_1$ to $C_4$ alkyl or $R^5$ and $R^6$ together with the nitrogen pendent thereto join to form a heterocyclic ring;

$R^2$ is selected from the group consisting of $C_1$ to $C_4$ alkyl, $C_2$ to $C_4$ alkenyl, and $C_2$ to $C_4$ alkynyl; and $R^3$ and $R^4$ are independently $C_1$ to $C_3$ alkyl or $R^3$, $R^4$ together with the nitrogen atom pendent thereto join to form a heterocyclic ring;

or a pharmaceutically acceptable salt, ester, or prodrug thereof.

In another embodiment, the present invention provides a compound of formula II:

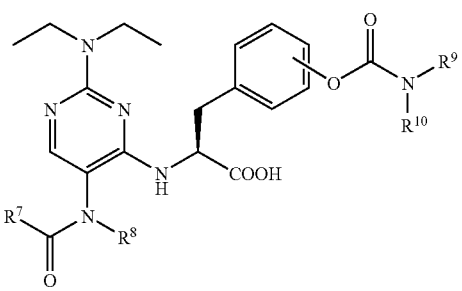

II wherein:

$R^7$ is $C_1$ to $C_4$ alkyl, $C_1$ to $C_4$ haloalkyl, or heteroaryl;

$R^8$ is $C_1$ to $C_4$ alkyl;

$R^9$ and $R^{10}$ are independently $C_1$ to $C_3$ alkyl or $R^9$, $R^{10}$ together with the nitrogen atom pendent thereto join to form a heterocyclic ring;

or a pharmaceutically acceptable salt, ester, or prodrug thereof.

In another embodiment, the present invention provides compounds of formula III:

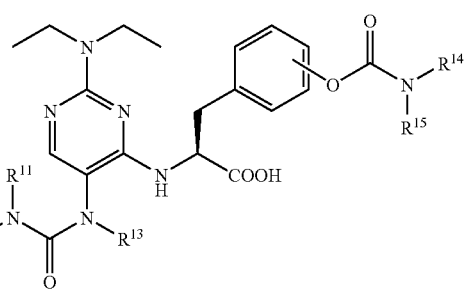

III wherein:

$R^{11}$ and $R^{12}$ are independently $C_1$ to $C_4$ alkyl or $R^{11}$ and $R^{12}$, together with the nitrogen atom pendent thereto, are joined to form a heterocyclic ring;

$R^{13}$ is $C_1$ to $C_4$ alkyl; and $R^{14}$ and $R^{15}$ are independently $C_1$ to $C_3$ alkyl or $R^{14}$ and $R^{15}$ together with the nitrogen atom pendent thereto join to form a heterocyclic ring;

or a pharmaceutically acceptable salt, ester, or prodrug thereof.

The present invention also provides the compounds in Table 4.

TABLE 4

| | Structure | Name |
|---|---|---|
| 1 | 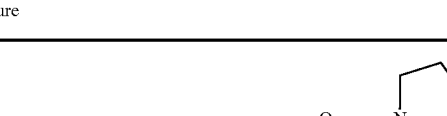 | N-[2-diethylamino-5-{N-ethyl-N-(trifluoroacetyl)amino}pyrimidin-4-yl]-L-4'-{(pyrrolidin-1-yl)carbonyloxy}phenylalanine |

TABLE 4-continued

| Structure | Name |
|---|---|
| 2 | N-[2-diethylamino-5-{N-ethyl-N-(iso-propylcarbonyl)amino}pyrimidin-4-yl]-L-4'-{(pyrrolidin-1-yl)carbonyloxy}phenylalanine |
| 3 | N-[2-dieethylamino-5-{N-ethyl-N-(t-butylcarbonyl)amino}pyrimidin-4-yl]-L-4'-{(pyrrolidin-1-yl)carbonyloxy}phenylalanine |
| 4 | N-[2-diethylamino-5-{N-ethyl-N-(furan-2-ylcarbonyl)amino}pyrimidin-4-yl]-L-4'-{(pyrrolidin-1-yl)carbonyloxy}phenylalanine |
| 5 | N-[2-diethylamino-5-{N-ethyl-N-(piperidin-1-ylcarbonyl)amino}pyrimidin-4-yl]-L-4'-{(pyrrrolidin-1-yl)carbonyloxy}phenylalanine |

TABLE 4-continued

| Structure | Name |
|---|---|
| 6 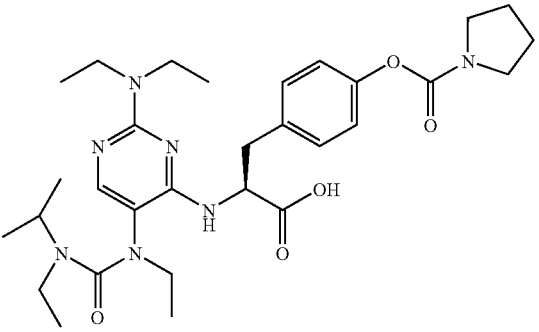 | N-[2-diethylamino-5-{N-ethyl-N-(N-ethyl-N-iso-propylaminocarbonyl)amino}pyrimidin-4-yl]-L-4'-{(pyrrolidin-1-yl)carbonyloxy}phenylalanine |
| 7 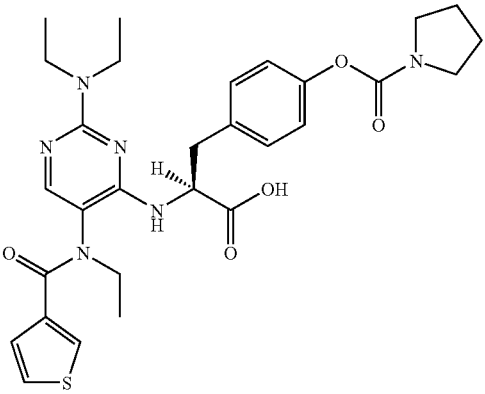 | N-[2-diethylamino-5-{N-ethyl-N-(thien-3-ylcarbonyl)amino}pyrimidin-4-yl]-L-4'-{(pyrrolidin-1-yl)carbonyloxy}phenylalanine |
| 8 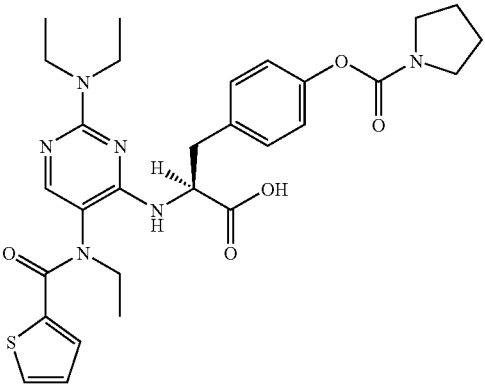 | N-[2-diethylamino-5-{N-ethyl-N-(thien-2-ylcarbonyl)amino}pyrimidin-4-yl]-L-4'-{(pyrrolidin-1-yl)carbonyloxy}phenylalanine |
| 9 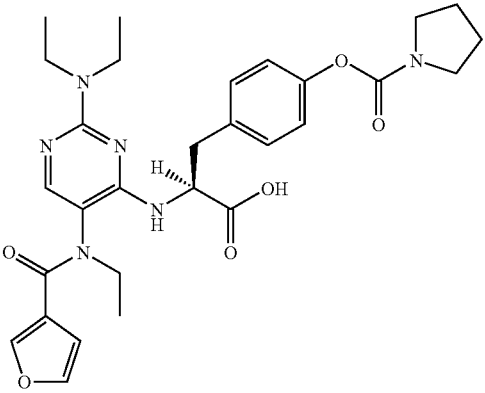 | N-[2-diethylamino-5-{N-ethyl-N-(furan-3-ylcarbonyl)amino}pyrimidin-4-yl]-L-4'-{(pyrrolidin-1-yl)carbonyloxy}phenylalanine |

TABLE 4-continued

| Structure | Name |
|---|---|
| 10 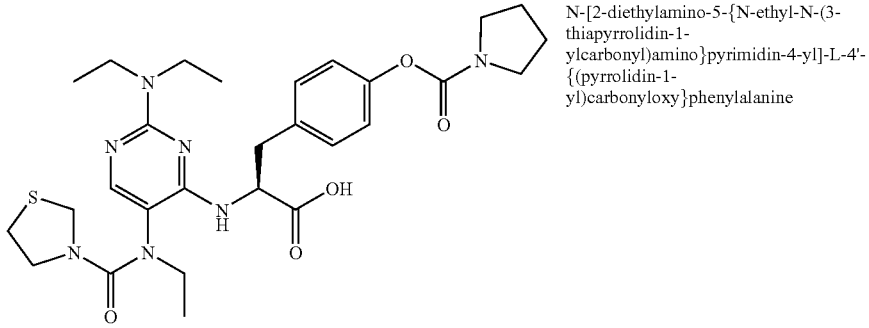 | N-[2-diethylamino-5-{N-ethyl-N-(3-thiapyrrolidin-1-ylcarbonyl)amino}pyrimidin-4-yl]-L-4'-{(pyrrolidin-1-yl)carbonyloxy}phenylalanine |
| 11 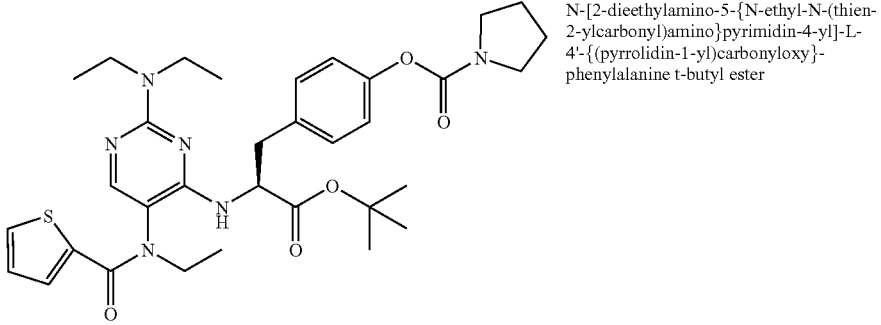 | N-[2-dieethylamino-5-{N-ethyl-N-(thien-2-ylcarbonyl)amino}pyrimidin-4-yl]-L-4'-{(pyrrolidin-1-yl)carbonyloxy}-phenylalanine t-butyl ester |
| 12 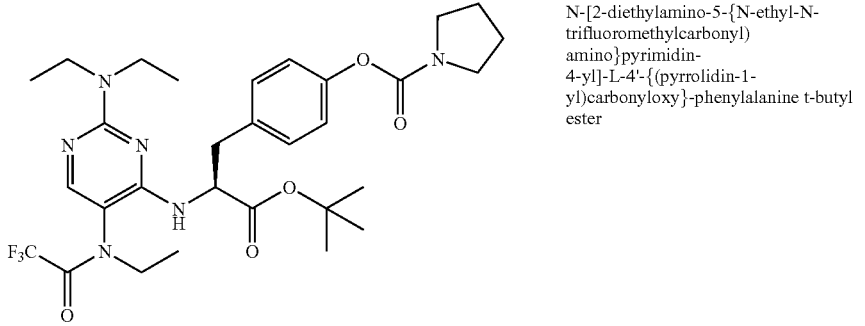 | N-[2-diethylamino-5-{N-ethyl-N-trifluoromethylcarbonyl)amino}pyrimidin-4-yl]-L-4'-{(pyrrolidin-1-yl)carbonyloxy}-phenylalanine t-butyl ester |
| 13 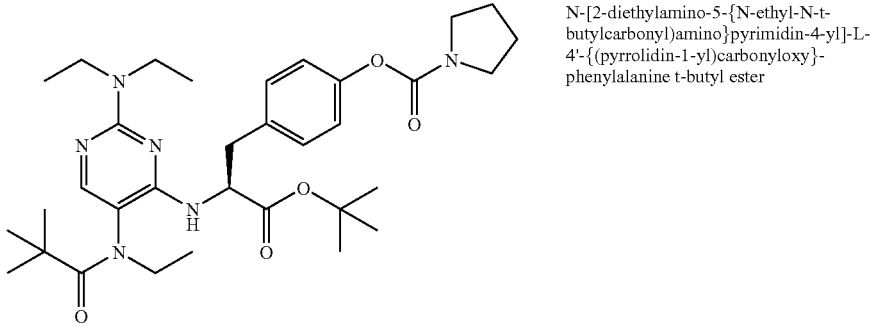 | N-[2-diethylamino-5-{N-ethyl-N-t-butylcarbonyl)amino}pyrimidin-4-yl]-L-4'-{(pyrrolidin-1-yl)carbonyloxy}-phenylalanine t-butyl ester |

TABLE 4-continued

| Structure | Name |
|---|---|
| 14 | N-[2-diethylamino-5-{N-ethyl-N-furan-3-ylcarbonyl)amino}pyrimidin-4-yl]-L-4'-{(pyrrolidin-1-yl)carbonyloxy}-phenylalanine t-butyl ester |

DETAILED DESCRIPTION OF THE INVENTION

As above, this invention relates to compounds which inhibit leukocyte adhesion and, in particular, leukocyte adhesion mediated at least in part by α4 integrins, preferably VLA-4. However, prior to describing this invention in further detail, the following terms will first be defined.

Definitions

Unless otherwise stated, the following terms used in the specification and claims have the meanings given below:

As used herein and unless otherwise defined, "alkyl" refers to straight, branched and cyclic alkyl groups preferably having from 1 to 4 carbon atoms and more preferably 1 to 3 carbon atoms. This term is exemplified by groups such as methyl, ethyl, n-propyl, iso-propyl, n-butyl, iso-butyl, sec-butyl, t-butyl, cyclopropyl, cyclobutyl, and methylene-cyclopropyl.

"Alkenyl" refers to straight and branched alkenyl group having from 2 to 4 carbon atoms and preferably 2 to 3 carbon atoms and having at least 1 and preferably 1 site of alkenyl unsaturation. Examples of such alkenyl groups include vinyl (—CH=CH$_2$), allyl (—CH$_2$CH=CH$_2$), n-propen-1-yl (—CH=CHCH$_3$), n-buten-2-yl (—CH$_2$CH=CHCH$_3$), and the like. Included within this term are the cis and trans isomers or mixtures of these isomers.

"Alkynyl" refers to straight and branched alkynyl group having from 2 to 4 carbon atoms and preferably 2 to 3 carbon atoms and having at least 1 and preferably 1 site of alkynyl unsaturation. Examples of such alkynyl groups include acetylenyl (—C≡CH), propargyl (—CH$_2$C≡CH), n-propyn-1-yl (—CH=CHCH$_3$), and the like.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryls include phenyl and naphthyl.

"Substituted aryl" refers to aryl groups which are substituted with from 1 to 3 substituents, and preferably 1 to 2 substituents, selected from the group consisting of hydroxyl, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, carboxyl, carboxyl esters, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, halo, nitro, heteroaryl, substituted heteroaryl, heterocyclic, substituted heterocyclic, heteroaryloxy, substituted heteroaryloxy, heterocyclyloxy, substituted heterocyclyloxy, amino sulfonyl (NH$_2$—SO$_2$—), and substituted amino sulfonyl.

"Halo" or "halogen" refers to fluoro, chloro, bromo and iodo and preferably is either fluoro or chloro.

"Haloalkyl" refers to alkyl groups having from 1 to 5 halo groups. Preferably, such groups have from 1 to 3 halo groups and 1 to 2 carbon atoms. Particularly preferred haloalkyl groups include trihalomethyl (e.g., trifluoromethyl) and trihaloethyl (e.g., 2,2,2-trifluoroeth-1-yl).

"Heteroaryl" refers to an aromatic carbocyclic group of from 2 to 10 carbon atoms and 1 to 4 heteroatoms selected from oxygen, nitrogen and sulfur within the ring. Such heteroaryl groups can have a single ring (e.g., pyridyl or furyl) or multiple condensed rings wherein the condensed ring may be aryl or heteroaryl. Examples of such heteroaryls include, for instance, furan-2-yl, furan-3-yl, thien-2-yl, thien-3-yl, pyrrol-2-yl, pyrrol-3-yl, pyridyl (2-, 3-, and 4-pyridyls) and the like. In one embodiment, the sulfur and/or nitrogen atoms of the heteroaryl are optionally oxidized (i.e., —S(O)— or —S(O)$_2$—, and/or N-oxides).

"Heterocycle" or "heterocyclic" refers to a saturated or unsaturated non-herteroaromatic group having a single ring or multiple condensed rings, from 1 to 10 carbon atoms and from 1 to 4 hetero atoms selected from nitrogen, sulfur or oxygen within the ring wherein, in fused ring systems, one or more the rings can be aryl or heteroaryl. In one embodiment, the sulfur and/or nitrogen atoms of the heterocycle are optionally oxidized (i.e., —S(O)— or —S(O)$_2$—, and/or N-oxides).

"Pharmaceutically acceptable carrier" means a carrier that is useful in preparing a pharmaceutical composition that is generally safe, non-toxic and neither biologically nor otherwise undesirable, and includes a carrier that is acceptable for veterinary use as well as human pharmaceutical use. "A pharmaceutically acceptable carrier" as used in the specification and claims includes both one and more than one such carrier.

"Prodrug" refers to any pharmaceutically acceptable derivative of a compound of this invention that is capable of directly or indirectly providing a compound of this invention or an active metabolite or residue thereof when administered to a subject. Particularly favored derivatives and prodrugs are those that increase the bioavailability of the compounds of this invention when such compounds are administered to a subject (e.g., by allowing an orally administered compound to be more readily absorbed into the blood) or which enhance delivery of the parent compound to a biological compartment (e.g., the brain or lymphatic system) relative to the parent species. Prodrugs include ester forms of the compounds of the invention. Examples of ester prodrugs include formate, acetate, propionate, butyrate, acrylate, and ethylsuccinate derivatives. An general overview of prodrugs is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

"Pharmaceutically acceptable salt" refers to salts which retain the biological effectiveness and properties of the compounds of this invention and which are not biologically or otherwise undesirable. In many cases, the compounds of this invention are capable of forming acid and/or base salts by virtue of the presence of amino and/or carboxyl groups or groups similar thereto.

Pharmaceutically-acceptable base addition salts can be prepared from inorganic and organic bases. Salts derived from inorganic bases, include by way of example only, sodium, potassium, lithium, ammonium, calcium, and magnesium salts. Salts derived from organic bases include, but are not limited to, salts of primary, secondary, and tertiary amines, such as alkyl amines, dialkyl amines, trialkyl amines, substituted alkyl amines, di(substituted alkyl)amines, tri(substituted alkyl)amines, alkenyl amines, dialkenyl amines, trialkenyl amines, substituted alkenyl amines, di(substituted alkenyl)amines, tri(substituted alkenyl)amines, cycloalkyl amines, di(cycloalkyl)amines, tri(cycloalkyl)amines, substituted cycloalkyl amines, disubstituted cycloalkyl amine, trisubstituted cycloalkyl amines, cycloalkenyl amines, di(cycloalkenyl)amines, tri(cycloalkenyl)amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and triamines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Examples of suitable amines include, by way of example only, isopropylamine, trimethyl amine, diethyl amine, tri(isopropyl)amine, tri(n-propyl)amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in the practice of this invention, for example, carboxylic acid amides, including carboxamides, lower alkyl carboxamides, dialkyl carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The term "pharmaceutically-acceptable cation" refers to the cation of a pharmaceutically-acceptable salt.

It is understood that in all substituted groups defined herein, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to-substituted aryl-(substituted aryl)-(substituted aryl).

"Treating" or "treatment" of a disease includes:

(1) preventing the disease, i.e., causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Pharmaceutically acceptable salt" refers to pharmaceutically acceptable salts of a compound of formula I which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

Integrins are a large-family of homologous transmembrane linker proteins that are the principal receptors on animal cells for binding most extracellular matrix proteins, such as collagen, fibronectin, and laminin. The integrins are heterodimers comprised of an α chain and a β chain. To date, twenty different integrin heterodimers, made from 9 different α subunits and 14 different β subunits, have been identified. The term "α4 integrins" refers to the class of heterodimer, enzyme-linked cell-surface receptors that contain the α4 subunit paired with any of the β subunits. VLA-4 is an example of an α4 integrin, and is a heterodimer of the α4 and β1 subunits, and is also referred to as α4β1 integrin.

This invention provides compounds, pharmaceutically acceptable salts thereof, compositions thereof, syntheses thereof, and methods for treating VLA-4 mediated diseases.

In one embodiment, the present invention provides compounds of formula I:

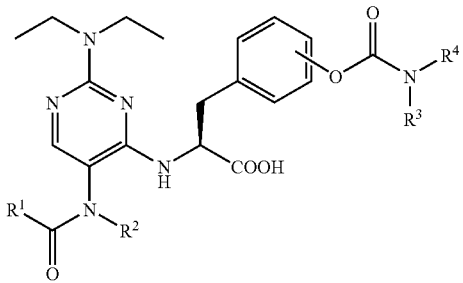

wherein:

$R^1$ is selected from the group consisting of $C_1$ to $C_4$ alkyl, $C_1$ to $C_4$ haloalkyl, heteroaryl and —N($R^5$)($R^6$) where $R^5$ and $R^6$ are independently selected from the group consisting of hydrogen, $C_1$ to $C_4$ alkyl or $R^5$ and $R^6$ together with the nitrogen pendent thereto join to form a heterocyclic ring;

$R^2$ is selected from the group consisting of $C_1$ to $C_4$ alkyl, $C_2$ to $C_4$ alkenyl, and $C_2$ to $C_4$ alkynyl; and $R^3$ and $R^4$ are independently $C_1$ to $C_3$ alkyl or $R^3$, $R^4$ together with the nitrogen atom pendent thereto join to form a heterocyclic ring;

or a pharmaceutically acceptable salt, ester, or prodrug thereof.

In some embodiments, the —OC(O)NR$^3$R$^4$ group is in the para position of the phenyl ring.

In some embodiments, $R^3$ and $R^4$ are joined to form a heterocyclic ring. In other embodiments, $R^3$ and $R^4$ are joined to form a pyrrolidinyl ring.

In some embodiments, $R^3$ is $C_1$ to $C_4$ alkyl. In other embodiments, $R^2$ is ethyl.

In still other embodiments, $R^3$ and $R^4$ are joined to form a heterocyclic ring and $R^2$ is $C_1$ to $C_4$ alkyl. In yet other embodiments, $R^3$ and $R^4$ are joined to form a pyrrolidinyl ring and $R^2$ is ethyl.

Examples of compounds of this invention include those having the $R^1$, $R^2$, $R^3$, and $R^4$ groups recited in Table 1.

TABLE 1

| $R^1$ | $R^2$ | $R^3$ | $R^4$ |
|---|---|---|---|
| trifluoromethyl | ethyl | $R^3$ and $R^4$ together with the pendent nitrogen form a pyrrolidine ring | |
| iso-propyl | ethyl | $R^3$ and $R^4$ together with the pendent nitrogen form a pyrrolidine ring | |
| t-butyl | ethyl | $R^3$ and $R^4$ together with the pendent nitrogen form a pyrrolidine ring | |
| furan-2-yl | ethyl | $R^3$ and $R^4$ together with the pendent nitrogen form a pyrrolidine ring | |
| piperidin-1-yl | ethyl | $R^3$ and $R^4$ together with the pendent nitrogen form a pyrrolidine ring | |
| N-ethyl-N-iso-propylamino | ethyl | $R^3$ and $R^4$ together with the pendent nitrogen form a pyrrolidine ring | |
| thien-3-yl | ethyl | $R^3$ and $R^4$ together with the pendent nitrogen form a pyrrolidine ring | |
| thien-2-yl | ethyl | $R^3$ and $R^4$ together with the pendent nitrogen form a pyrrolidine ring | |
| furan-3-yl | ethyl | $R^3$ and $R^4$ together with the pendent nitrogen form a pyrrolidine ring | |
| 3-thiapyrrolidin-1-yl | ethyl | $R^3$ and $R^4$ together with the pendent nitrogen form a pyrrolidine ring | |

In another embodiment, the present invention provides a compound of formula II:

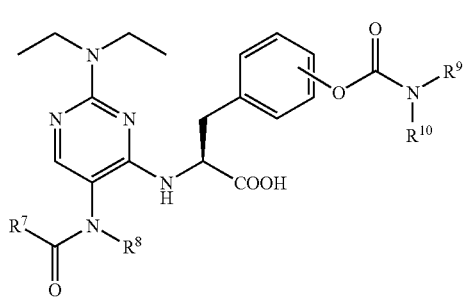

II wherein:

$R^7$ is $C_1$ to $C_4$ alkyl, $C_1$ to $C_4$ haloalkyl, or heteroaryl;

$R^8$ is $C_1$ to $C_4$ alkyl;

$R^9$ and $R^{10}$ are independently $C_1$ to $C_3$ alkyl or $R^9$, $R^{10}$ together with the nitrogen atom pendent thereto join to form a heterocyclic ring;

or a pharmaceutically acceptable salt, ester, or prodrug thereof.

In some embodiments, the —OC(O)NR$^9$R$^{10}$ group is in the para position of the phenyl ring.

In some embodiments, $R^9$ and $R^{10}$ are joined to form a heterocyclic ring. In other embodiments, $R^9$ and $R^{10}$ are joined to form a pyrrolidinyl ring.

In some embodiments, $R^8$ is $C_1$ to $C_4$ alkyl. In other embodiments, $R^8$ is ethyl.

In some embodiments, $R^7$ is $C_1$ to $C_4$ alkyl. In other embodiments, $R^7$ is selected from the group consisting of isopropyl and t-butyl.

In some embodiments, $R^7$ is $C_1$ to $C_4$ haloalkyl. In other embodiments $R^7$ is trifluoromethyl.

In some embodiments, $R^7$ is heteroaryl. In other embodiments, $R^7$ is selected from the group consisting of furan-2-yl, furan-3-yl, thien-2-yl, and thien-3-yl.

In some embodiments, $R^9$ and $R^{10}$ are joined to form a heterocyclic ring, $R^8$ is $C_1$ to $C_4$ alkyl, and $R^7$ is heteroaryl. In other embodiments, $R^9$ and $R^{10}$ together with the pendent nitrogen form a pyrrolidine ring, $R^8$ is ethyl, and $R^7$ is heteroaryl.

In some embodiments, $R^9$ and $R^{10}$ are joined to form a heterocyclic ring, $R^8$ is $C_1$ to $C_4$ alkyl, and $R^7$ is alkyl. In other embodiments, $R^9$ and $R^{10}$ together with the pendent nitrogen form a pyrrolidine ring, $R^8$ is ethyl, and $R^7$ is alkyl.

The present invention further provides the compounds of Formula II having the $R^7$, $R^8$, $R^9$, and $R^{10}$ groups recited in Table 2.

TABLE 2

| $R^7$ | $R^8$ | $R^9$ | $R^{10}$ |
|---|---|---|---|
| trifluoromethyl | ethyl | $R^9$ and $R^{10}$ together with the pendent nitrogen form a pyrrolidine ring | |
| iso-propyl | ethyl | $R^9$ and $R^{10}$ together with the pendent nitrogen form a pyrrolidine ring | |
| t-butyl | ethyl | $R^9$ and $R^{10}$ together with the pendent nitrogen form a pyrrolidine ring | |
| furan-2-yl | ethyl | $R^9$ and $R^{10}$ together with the pendent nitrogen form a pyrrolidine ring | |
| thien-3-yl | ethyl | $R^9$ and $R^{10}$ together with the pendent nitrogen form a pyrrolidine ring | |
| thien-2-yl | ethyl | $R^9$ and $R^{10}$ together with the pendent nitrogen form a pyrrolidine ring | |
| furan-3-yl | ethyl | $R^9$ and $R^{10}$ together with the pendent nitrogen form a pyrrolidine ring | |

In another embodiment, the present invention provides compounds of formula III:

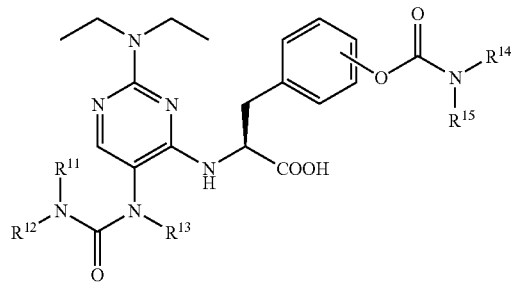

III wherein:

$R^1$ and $R^{12}$ are independently $C_1$ to $C_4$ alkyl or $R^{11}$ and $R^{12}$, together with the nitrogen atom pendent thereto, are joined to form a heterocyclic ring;

$R^{13}$ is $C_1$ to $C_4$ alkyl; and $R^{14}$ and $R^{15}$ are independently $C_1$ to $C_3$ alkyl or $R^{14}$ and $R^{15}$ together with the nitrogen atom pendent thereto join to form a heterocyclic ring;

or a pharmaceutically acceptable salt, ester, or prodrug thereof.

In some embodiments, the —OC(O)NR$^{14}$R$^{15}$ group is in the para position of the phenyl ring.

In some embodiments, $R^{14}$ and $R^{15}$ are joined to form a heterocyclic ring. In other embodiments, $R^{14}$ and $R^{15}$ are joined to form a pyrrolidinyl ring.

In some embodiments, $R^{13}$ is $C_1$ to $C_4$ alkyl. In other embodiments, $R^{13}$ is ethyl.

In some embodiments, $R^{11}$ and $R^{12}$ are independently $C_1$ to $C_4$ alkyl. In other embodiments $R^{11}$ is ethyl and $R^{12}$ is isopropyl.

In some embodiments, $R^{11}$ and $R^{12}$, together with the nitrogen atom pendent thereto, are joined to form a heterocyclic ring. In other embodiments, the heterocyclic ring is selected from the group consisting of piperidin-1-yl and 3-thiapyrrolidin-1-yl.

In yet other embodiments, $R^{14}$ and $R^{15}$ are joined to form a heterocyclic ring, $R^{13}$ is $C_1$ to $C_4$ alkyl, and $R^{11}$ and $R^{12}$, together with the nitrogen atom pendent thereto, are joined to form a heterocyclic ring.

The present invention further provides compounds of formula III having the $R^{11}$, $R^{12}$, $R^{13}$, $R^4$, and $R^{15}$ groups recited in Table 3.

TABLE 3

| $R^{11}$ | $R^{12}$ | $R^{13}$ | $R^{14}$ | $R^{15}$ |
|---|---|---|---|---|
| $R^{11}$ and $R^{12}$ together with the pendent nitrogen form a piperidine ring | | ethyl | | $R^{14}$ and $R^{15}$ together with the pendent nitrogen form a pyrrolidine ring |
| iso-propyl | ethyl | ethyl | | $R^{14}$ and $R^{15}$ together with the pendent nitrogen form a pyrrolidine ring |
| $R^{11}$ and $R^{12}$ together with the pendent nitrogen form a 3-thiapyrrolidine ring | | ethyl | | $R^{14}$ and $R^{15}$ together with the pendent nitrogen form a pyrrolidine ring |

In some embodiments, the present invention provides compounds of formula I, II, and III having the carbamyl substituents:

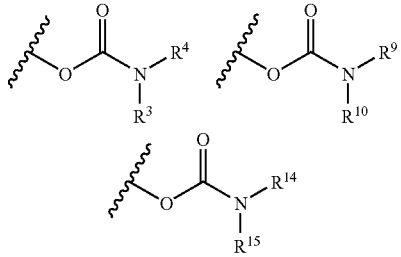

in their respective formulae attached to the phenyl ring at the para position. In still other embodiments, the compounds in Tables 1, 2, and 3 have the carbamyl substituents attached at the para position.

In some embodiments, the present invention also provides compounds of formula I, II, and III, including those in Tables 1, 2, and 3, having the carbamyl substituents attached at the ortho or meta positions.

The present invention also provides the compounds in Table 4.

TABLE 4

| | Structure | Name |
|---|---|---|
| 1 | 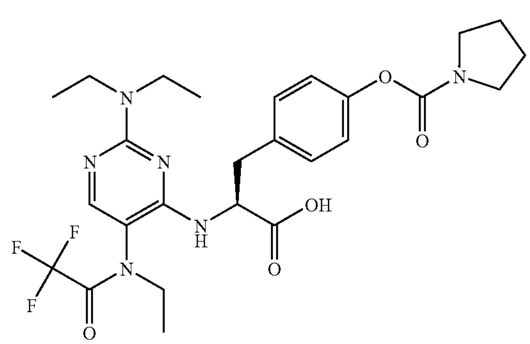 | N-[2-diethylamino-5-{N-ethyl-N-(trifluoroacetyl)amino}pyrimidin-4-yl]-L-4'-{Z(pyrrolidin-1-yl)carbonyloxy}phenylalanine |

TABLE 4-continued

| Structure | Name |
|---|---|
| 2 | N-[2-diethylamino-5-{N-ethyl-N-(iso-propylcarbonyl)amino}pyrimidin-4-yl]-L-4'-{(pyrrolidin-1-yl)carbonyloxy}phenylalanine |
| 3 | N-[2-diethylamino-5-{N-ethyl-N-(t-butylcarbonyl)amino}pyrimidin-4-yl]-L-4'-{(pyrrolidin-1-yl)carbonyloxy}phenylalanine |
| 4 | N-[2-diethylamino-5-{N-ethyl-N-(furan-2-ylcarbonyl)amino}pyrimidin-4-yl]-L-4'-{(pyrrolidin-1-yl)carbonyloxy}phenylalanine |
| 5 | N-[2-diethylamino-5-{N-ethyl-N-(piperidin-1-ylcarbonyl)amino}pyrimidin-4-yl]-L-4'-{(pyrrolidin-1-yl)carbonyloxy}phenylalanine |

TABLE 4-continued

| Structure | Name |
|---|---|
| 6 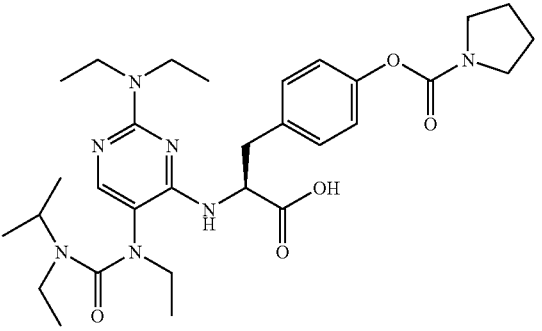 | N-[2-diethylamino-5-{N-ethyl-N-(N-ethyl-N-iso-propylaminocarbonyl)amino}pyrimidin-4-yl]-L-4'-{(pyrrolidin-1-yl)carbonyloxy}phenylalanine |
| 7 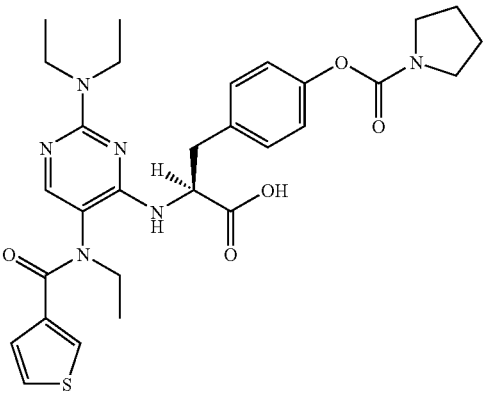 | N-[2-diethylamino-5-{N-ethyl-N-(thien-3-ylcarbonyl)amino}pyrimidin-4-yl]-L-4'-{(pyrrolidin-1-yl)carbonyloxy}phenylalanine |
| 8 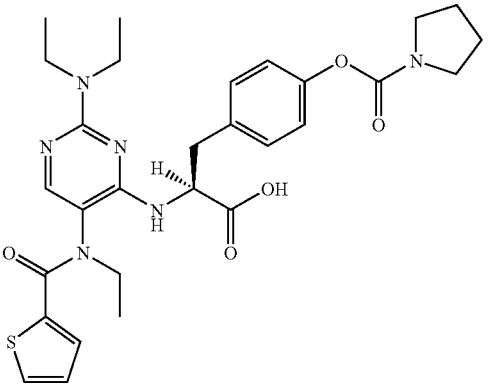 | N-[2-diethylamino-5-{N-ethyl-N-(thien-2-ylcarbonyl)amino}pyrimidin-4-yl]-L-4'-{(pyrrolidin-1-yl)carbonyloxy}phenylalanine |
| 9 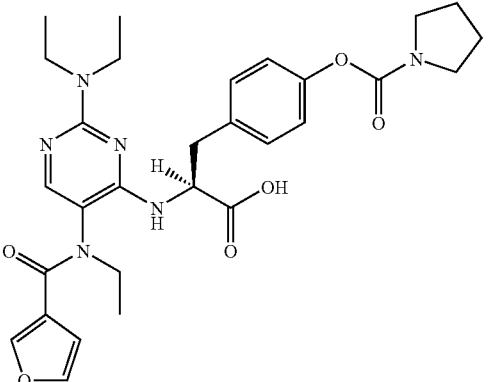 | N-[2-diethylamino-5-{N-ethyl-N-(furan-3-ylcarbonyl)amino}pyrimidin-4-yl]-L-4'-{(pyrrolidin-1-yl)carbonyloxy}phenylalanine |

TABLE 4-continued

| Structure | Name |
|---|---|
| 10 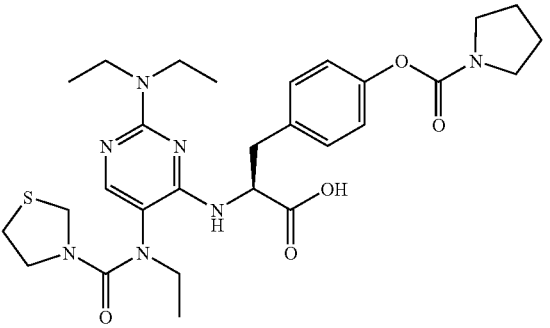 | N-[2-diethylamino-5-{N-ethyl-N-(3-thiapyrrolidin-1-ylcarbonyl)amino}pyrimidin-4-yl]-L-4'-{(pyrrolidin-1-yl)carbonyloxy}phenylalanine |
| 11 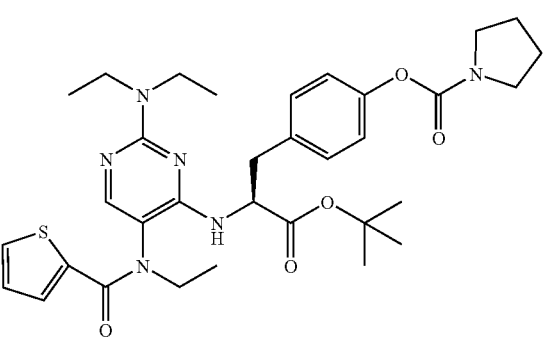 | N-[2-diethylamino-5-{N-ethyl-N-(thien-2-ylcarbonyl)amino}pyrimidin-4-yl]-L-4'-{(pyrrolidin-1-yl)carbonyloxy}-phenylalanine t-butyl ester |
| 12 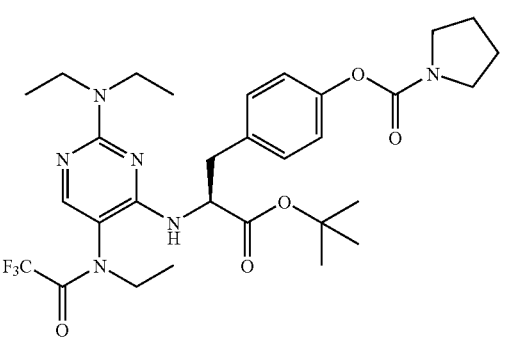 | N-[2-diethylamino-5-{N-ethyl-N-trifluoromethylcarbonyl)amino}pyrimidin-4-yl]-L-4'-{(pyrrolidin-1-yl)carbonyloxy}-phenylalanine t-butyl ester |
| 13 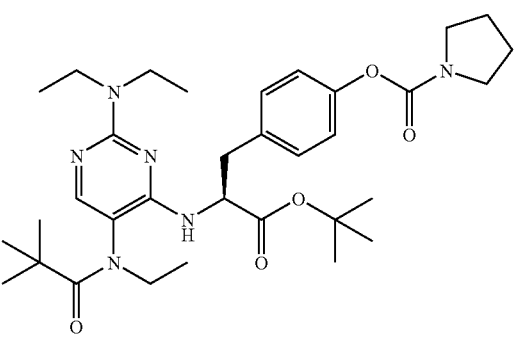 | N-[2-diethylamino-5-{N-ethyl-N-t-butylcarbonyl)amino}pyrimidin-4-yl]-L-4'-{(pyrrolidin-1-yl)carbonyloxy}-phenylalanine t-butyl ester |

TABLE 4-continued

| Structure | Name |
|---|---|
| 14 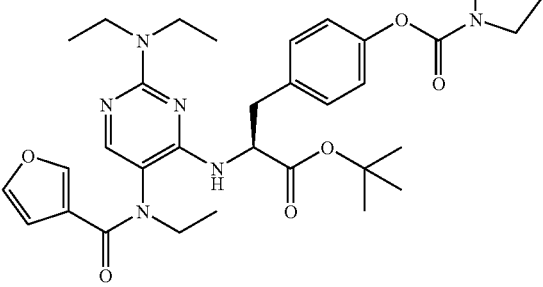 | N-[2-diethylamino-5-{N-ethyl-N-furan-3-ylcarbonyl)amino}pyrimidin-4-yl]-L-4'-{(pyrrolidin-1-yl)carbonyloxy}-phenylalanine t-butyl ester |

In another aspect, this invention provides pharmaceutical compositions comprising a pharmaceutically acceptable carrier and a therapeutically effective amount of one or more of the compounds defined herein.

In one of its method aspects, this invention is directed to a method for treating a disease mediated at least in part by α4 integrin, preferably VLA-4, in a patient, which method comprises administering a pharmaceutical composition comprising a pharmaceutically acceptable carrier and a therapeutically effective amount of one or more of the compounds of this invention.

The compounds and pharmaceutical compositions of this invention are useful for treating disease conditions mediated at least in part by α4 integrins, where the α4 integrin is preferably VLA-4 or leucocyte adhesion. Such disease conditions include, by way of example, asthma, Alzheimer's disease, atherosclerosis, AIDS dementia, diabetes (including acute juvenile onset diabetes), inflammatory bowel disease (including ulcerative colitis and Crohn's disease), multiple sclerosis, rheumatoid arthritis, tissue transplantation, tumor metastasis, meningitis, encephalitis, stroke, and other cerebral traumas, nephritis, retinitis, atopic dermatitis, psoriasis, myocardial ischemia and acute leukocyte-mediated lung injury such as that which occurs in adult respiratory distress syndrome.

Other disease conditions include, but are not limited to, inflammatory conditions such as erythema nodosum, allergic conjunctivitis, optic neuritis, uveitis, allergic rhinitis, Ankylosing spondylitis, psoriatic arthritis, vasculitis, Reiter's syndrome, systemic lupus erythematosus, progressive systemic sclerosis, polymyositis, dermatomyositis, Wegner's granulomatosis, aortitis, sarcoidosis, lymphocytopenia, temporal arteritis, pericarditis, myocarditis, congestive heart failure, polyarteritis nodosa, hypersensitivity syndromes, allergy, hypereosinophilic syndromes, Churg-Strauss syndrome, chronic obstructive pulmonary disease, hypersensitivity pneumonitis, chronic active hepatitis, interstitial cystitis, autoimmune endocrine failure, primary biliary cirrhosis, autoimmune aplastic anemia, chronic persistent hepatitis and thyroiditis.

In a preferred embodiment, the disease condition mediated by α4 integrin is an inflammatory disease.

Compounds of this invention include, by way of example, the following:

N-[2-diethylamino-5-{N-ethyl-N-(trifluoroacetyl) amino}pyrimidin-4-yl]-L-4'-{(pyrrolidin-1-yl) carbonyloxy}phenylalanine;

N-[2-diethylamino-5-{N-ethyl-N-(iso-propylcarbonyl) amino}pyrimidin-4-yl]-L-4'-{(pyrrolidin-1-yl) carbonyloxy}phenylalanine;

N-[2-diethylamino-5-{N-ethyl-N-(t-butylcarbonyl) amino}pyrimidin-4-yl]-L-4'-{(pyrrolidin-1-yl) carbonyloxy}phenylalanine;

N-[2-diethylamino-5-{N-ethyl-N-(furan-2-ylcarbonyl) amino} pyrimidin-4-yl]-L-4'-{(pyrrolidin-1-yl) carbonyloxy}phenylalanine;

N-[2-diethylamino-5-{N-ethyl-N-(piperidin-1-ylcarbonyl) amino}pyrimidin-4-yl]-L-4'-{(pyrrolidin-1-yl) carbonyloxy}phenylalanine;

N-[2-diethylamino-5-{N-ethyl-N-(N-ethyl-N-iso-propylaminocarbonyl)amino}-pyrimidin-4-yl]-L-4'-{(pyrrolidin-1-yl)carbonyloxy}phenylalanine;

N-[2-diethylamino-5-{N-ethyl-N-(thien-3-ylcarbonyl) amino} pyrimidin-4-yl]-L-4'-{(pyrrolidin-1-yl)carbonyloxy} phenylalanine;

N-[2-diethylamino-5-{N-ethyl-N-(thien-2-ylcarbonyl) amino} pyrimidin-4-yl]-L-4'-{(pyrrolidin-1-yl) carbonyloxy}phenylalanine;

N-[2-diethylamino-5-{N-ethyl-N-(furan-3-ylcarbonyl) amino} pyrimidin-4-yl]-L-4'-{(pyrrolidin-1-yl)carbonyloxy} phenylalanine;

N-[2-diethylamino-5-{N-ethyl-N-(3-thiapyrrolidin-1-ylcarbonyl)amino} pyrimidin-4-yl]-L-4'-{(pyrrolidin-1-yl) carbonyloxy}phenylalanine;

N-[2-diethylamino-5-{N-ethyl-N-(thien-2-ylcarbonyl) amino}pyrimidin-4-yl]-L-4'-{(pyrrolidin-1-yl)carbonyloxy}-phenylalanine t-butyl ester;

N-[2-diethylamino-5-{N-ethyl-N-trifluoromethylcarbonyl) amino} pyrimidin-4-yl]-L-4'-{(pyrrolidin-1-yl)carbonyloxy}-phenylalanine t-butyl ester;

N-[2-diethylamino-5-{N-ethyl-N-t-butylcarbonyl)amino} pyrimidin-4-yl]-L-4'-{(pyrrolidin-1-yl)carbonyloxy}-phenylalanine t-butyl ester; and N-[2-diethylamino-5-{N-ethyl-N-furan-3-ylcarbonyl) amino} pyrimidin-4-yl]-L-4'-{(pyrrolidin-1-yl)carbonyloxy}-phenylalanine t-butyl ester;

or the pharmaceutically acceptable salt, ester, or prodrug thereof.

Compound Preparation

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Second Edition, Wiley, New York, 1991, and references cited therein.

Furthermore, the compounds of this invention will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

In one embodiment, the compounds of this invention can be prepared as described below in Scheme 1:

Scheme 1

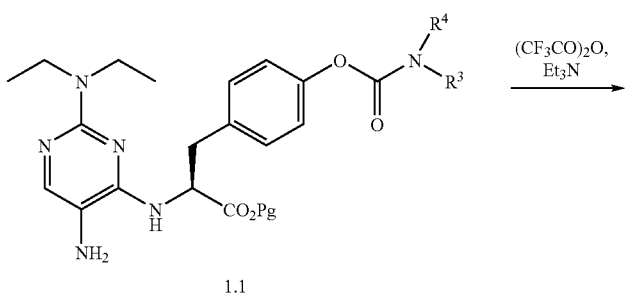

1.1

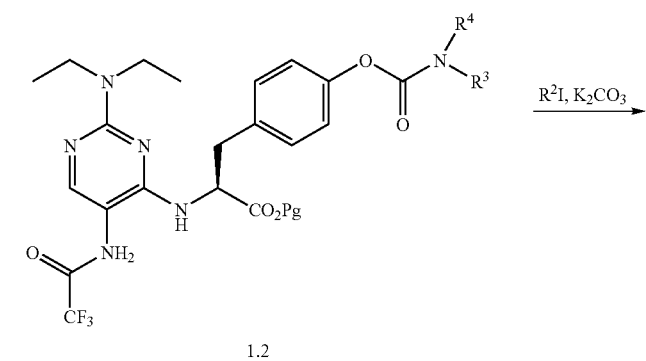

1.2

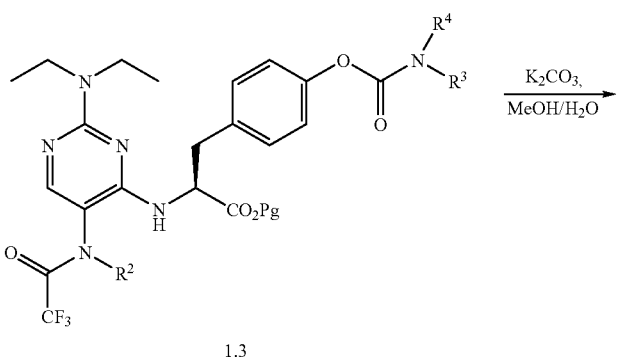

1.3

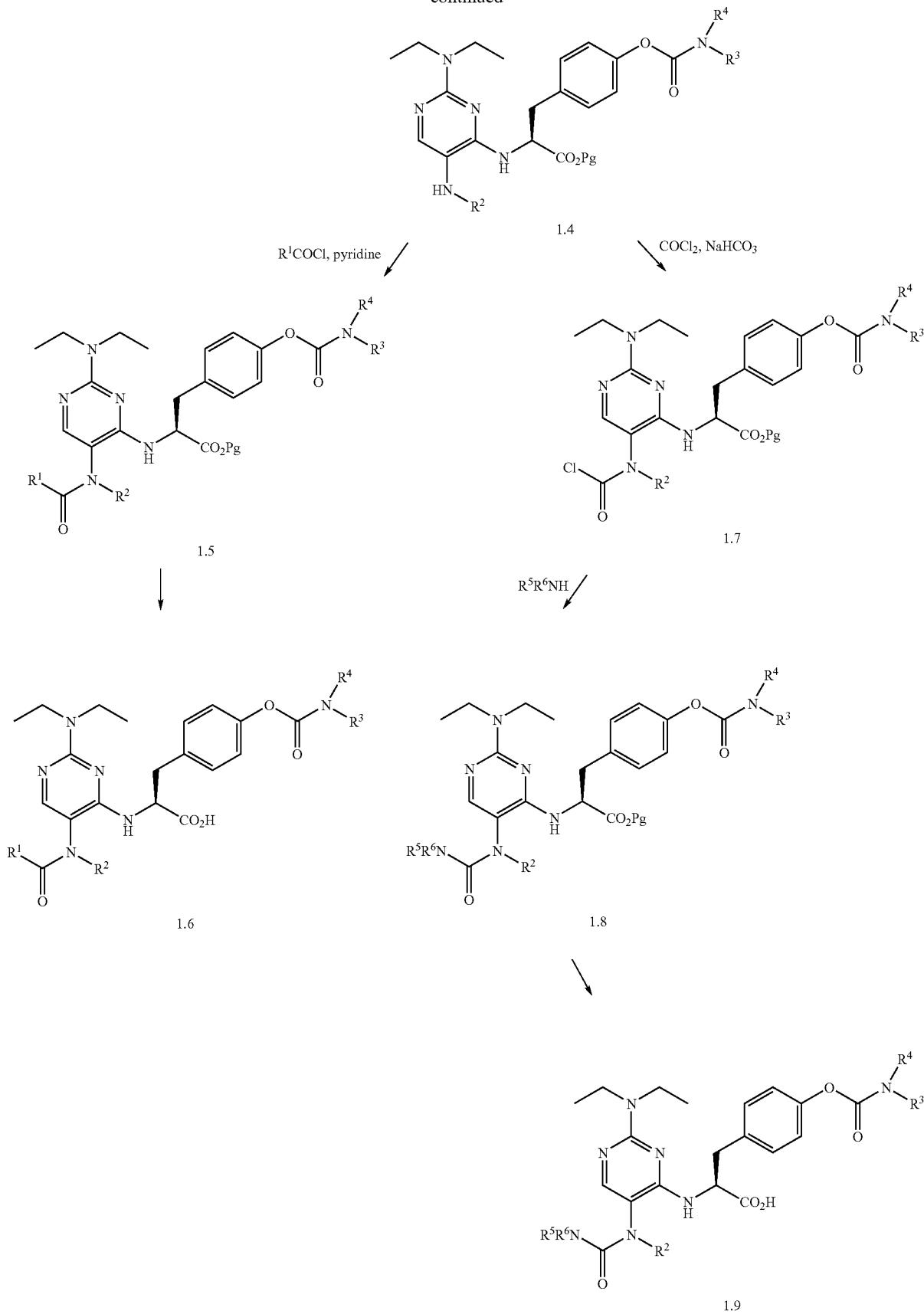

where $R^1$, $R^2$, $R^3$, $R^4$, $R^5$ and $R^6$ are as defined above and Pg is a carboxyl protecting group such as benzyl, t-butyl, and the like.

In Scheme 1, the starting 5-aminopyrimidine intermediates, compound 1.1, are described in detail in WO 03/099809, herein incorporated by reference in its entirety, and, for the sake of illustration only, are shown in this scheme as 4-substituted phenylalanine derivatives. It is understood, of course, that 2- and 3-substituted phenylalanine derivatives would follow a similar reaction pathway.

Specifically, in Scheme 1,5-amino-2-diethylamino-4-substituted pyrimidine, compound 1.1 (prepared from by corresponding 5-nitro-pyrimidine by reduction with 5% Pd/C or 5% $PtO_2$ by weight) is converted to the corresponding trifluoroacetamide, compound 1.2, by conventional methods. For example, a slight excess of trifluoroacetic anhydride is combined with compound 1.1 in a suitable inert diluent such as tetrahydrofuran, methylene chloride, pyridine, and the like. The reaction is maintained at from about 0° C. to about 30° C. until the reaction is substantially complete which typically occurs within about 0.5 to 24 hours. Upon completion of the reaction, the compound 1.2 is recovered by conventional methods including neutralization, evaporation, extraction, precipitation, chromatography, filtration, and the like or, alternatively, is employed in the next step without purification and/or isolation.

Conversion of compound 1.2 to the corresponding $N(R^2)$, N-trifluoroacetamidopyrimidine, compound 1.3, again proceeds via conventional techniques. For example, an excess of the halide, $R^2$—I, is combined with compound 1.2 in a suitable inert diluent such as DMF in the presence of an excess of a suitable base such as potassium carbonate. In a preferred embodiment, approximately two equivalents of $R^2$—I and potassium carbonate are employed. The reaction is maintained under ambient conditions in a sealed container and is continued until the reaction is substantially complete which typically occurs in 20-72 hours. Upon completion of the reaction, the compound 1.3 is recovered by conventional methods including neutralization, evaporation, extraction, precipitation, chromatography, filtration, and the like or, alternatively, is employed in the next step without purification and/or isolation.

The carboxyl protecting group of compound 1.3 can be removed by conventional conditions to provide for a compound of Formula I (not shown). In one embodiment, a t-butyl protecting group can be removed by contact with formic acid. In another embodiment, a benzyl protecting group can be removed by contact with hydrogen in the presence of a palladium/carbon catalyst typically in a protic solvent such as methanol under elevated hydrogen pressures.

Alternatively, the trifluoroacetyl group can be removed to provide for the corresponding amine, compound 1.4. In this embodiment, the trifluoroacetyl group acts as an amine protecting group. As above, this reaction conventionally proceeds, for example, by contacting compound 1.3 with a large excess of a suitable base such as potassium carbonate in a mixture of water and a protic solvent such as methanol. The reaction is conducted at elevated temperatures such as 40° to 60° C. and is continued until the reaction is substantially complete. Upon completion of the reaction, the compound 1.4 is recovered by conventional methods including neutralization, evaporation, extraction, precipitation, chromatography, filtration, and the like or, alternatively, is employed in the next step without purification and/or isolation.

In Scheme 1, compound 1.4 can be used to prepare either urea derivatives where $R^1$=—$NR^5R^6$ or acylamino derivatives where $R^1$ is $C_1$ to $C_4$ alkyl, $C_1$ to $C_4$ haloalkyl or heteroaryl bound to the carbonyl group other than through a nitrogen atom. In the first embodiment, urea derivatives are prepared by conventional methods such as by first preparing the amido chloride, compound 1.7. This compound is prepared by contacting compound 1.4 with an excess of phosgene in the presence of a suitable base such as potassium carbonate, potassium bicarbonate, sodium carbonate, and the like. Upon completion of the reaction, compound 1.7 can be recovered by conventional methods including neutralization, evaporation, extraction, precipitation, chromatography, filtration, and the like but preferably is employed in the next step without purification and/or isolation.

Amido chloride, compound 1.7, is then converted to the corresponding urea derivative, compound 1.8, by reaction with a suitable amine, $R^5R^6NH$, under conventional conditions. Preferably, the reaction an equimolar amount or excess of the amine is contacted with compound 1.7 in a suitable solvent such tetrahydrofuran, dioxane, chloroform and the like. Upon completion of the reaction, compound 1.8 can be recovered by conventional methods including neutralization, evaporation, extraction, precipitation, chromatography, filtration, and the like or, alternatively, is employed in the next step without purification and/or isolation.

The carboxyl protecting group of compound 1.8 can be removed by conventional conditions to provide for compound 1.9, a compound of Formula I. In one embodiment, a t-butyl protecting group can be removed by contact with formic acid. In another embodiment, a benzyl protecting group can be removed by contact with hydrogen in the presence of a palladium/carbon catalyst typically in a protic solvent such as methanol under elevated hydrogen pressures. Upon completion of the reaction, compound 1.9 can be recovered by conventional methods including neutralization, evaporation, extraction, precipitation, chromatography, filtration, and the like.

In the second embodiment, acylamino derivatives, compound 1.5, are prepared by contacting compound 1.4 with a slight excess of an acyl halide in the presence of a suitable base such as triethylamine, diisopropylethylamine and the like in order to scavenge the acid generated. The reaction is preferably conducted in a suitable inert solvent such as tetrahydrofuran, dioxane, chloroform and the like. The reaction is preferably conducted at from about 0° to 30° C. and is continued until the reaction is substantially complete which typically occurs in 2-48 hours. Upon completion of the reaction, compound 1.5 can be recovered by conventional methods including neutralization, evaporation, extraction, precipitation, chromatography, filtration, and the like or, alternatively, is employed in the next step without purification and/or isolation.

The carboxyl protecting group of compound 1.5 can be removed by conventional conditions to provide for compound 1.6, a compound of Formula I. In one embodiment, a t-butyl protecting group can be removed by contact with formic acid. In another embodiment, a benzyl protecting group can be removed by contact with hydrogen in the presence of a palladium/carbon catalyst typically in a protic solvent such as methanol under elevated hydrogen pressures. Upon completion of the reaction, compound 1.6 can be recovered by conventional methods including neutralization, evaporation, extraction, precipitation, chromatography, filtration, and the like.

Pharmaceutical Formulations

When employed as pharmaceuticals, the compounds of this invention are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the compounds of Formula I-III above associated with pharmaceutically acceptable carriers. In making the compositions of this invention, the active ingredient is usually mixed with an excipient, diluted by an excipient or enclosed within such a carrier which can be in the form of a capsule, sachet, paper or other container. The excipient employed is typically an excipient suitable for administration to human subjects or other mammals. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

Administration of therapeutic agents by intravenous formulation is well known in the pharmaceutical industry. An intravenous formulation should possess certain qualities aside from being just a composition in which the therapeutic agent is soluble. For example, the formulation should promote the overall stability of the active ingredient(s), also, the manufacture of the formulation should be cost effective. All of these factors ultimately determine the overall success and usefulness of an intravenous formulation.

Other accessory additives that may be included in pharmaceutical formulations of compounds of the present invention as follow: solvents: ethanol, glycerol, propylene glycol; stabilizers: ethylene diamine tetraacetic acid (EDTA), citric acid; antimicrobial preservatives: benzyl alcohol, methyl paraben, propyl paraben; buffering agents: citric acid/sodium citrate, potassium hydrogen tartrate, sodium hydrogen tartrate, acetic acid/sodium acetate, maleic acid/sodium maleate, sodium hydrogen phthalate, phosphoric acid/potassium dihydrogen phosphate, phosphoric acid/disodium hydrogen phosphate; and tonicity modifiers: sodium chloride, mannitol, dextrose.

The presence of a buffer may be necessary to maintain the aqueous pH in the range of from about 4 to about 8 and more preferably in a range of from about 4 to about 6. The buffer system is generally a mixture of a weak acid and a soluble salt thereof, e.g., sodium citrate/citric acid; or the monocation or dication salt of a dibasic acid, e.g., potassium hydrogen tartrate; sodium hydrogen tartrate, phosphoric acid/potassium dihydrogen phosphate, and phosphoric acid/disodium hydrogen phosphate.

The amount of buffer system used is dependent on (1) the desired pH; and (2) the amount of drug. Generally, the amount of buffer used is in a 0.5:1 to 50:1 mole ratio of buffer:drug (where the moles of buffer are taken as the combined moles of the buffer ingredients, e.g., sodium citrate and citric acid) of formulation to maintain a pH in the range of 4 to 8 and generally, a 1:1 to 10:1 mole ratio of buffer (combined) to drug present is used.

One useful buffer in the invention is sodium citrate/citric acid in the range of 5 to 50 mg per mL of sodium citrate to 1 to 15 mg per mL of citric acid, sufficient to maintain an aqueous pH of 4-6 of the composition.

The buffer agent may also be present to prevent the precipitation of the drug through soluble metal complex formation with dissolved metal ions, e.g., Ca, Mg, Fe, Al, Ba, which may leach out of glass containers or rubber stoppers or be present in ordinary tap water. The agent may act as a competitive complexing agent with the drug and produce a soluble metal complex leading to the presence of undesirable particulates.

In addition, the presence of an agent, e.g., sodium chloride in an amount of about of 1-8 mg/mL, to adjust the tonicity to the same value of human blood may be required to avoid the swelling or shrinkage of erythrocytes upon administration of the intravenous formulation leading to undesirable side effects such as nausea or diarrhea and possibly to associated blood disorders. In general, the tonicity of the formulation matches that of human blood which is in the range of 282 to 288 mOsm/kg, and in general is 285 mOsm/kg, which is equivalent to the osmotic pressure corresponding to a 0.9% solution of sodium chloride.

The intravenous formulation can be administered by direct intravenous injection, i.v. bolus, or can be administered by infusion by addition to an appropriate infusion solution such as 0.9% sodium chloride injection or other compatible infusion solution.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices which deliver the formulation in an appropriate manner.

The following formulation examples illustrate the pharmaceutical compositions of the present invention.

Formulation Example 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |

The active ingredient, starch, and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, starch and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ml dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425.0 mg quantities.

Formulation Example 9

A subcutaneous formulation may be prepared as follows:

| Ingredient | Quantity |
|---|---|
| Active Ingredient | 5.0 mg |
| Corn Oil | 1.0 mL |

Formulation Example 10

A topical formulation may be prepared as follows:

| Ingredient | Quantity |
|---|---|
| Active Ingredient | 1-10 g |
| Emulsifying Wax | 30 g |
| Liquid Paraffin | 20 g |
| White Soft Paraffin to | 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Example 11

An intravenous formulation may be prepared as follows:

| Ingredient | Quantity |
|---|---|
| Active Ingredient | 250 mg |
| Isotonic saline | 1000 mL |

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxyl, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Other suitable formulations for use in the present invention can be found in Remington's Pharmaceutical Sciences, Mace Publishing Company, Philadelphia, Pa., 17th ed. (1985).

As noted above, the compounds described herein are suitable for use in a variety of drug delivery systems described above. Additionally, in order to enhance the in vivo serum half-life of the administered compound, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

The conjugates of this invention are VLA-4 antagonists and are contemplated to provide enhanced in vivo retention as compared to the non-conjugated compounds. Such improved retention of the conjugate within the body would result in lower required dosages of the drug, which, in turn, would result in fewer side effects and reduced likelihood of toxicity. In addition, the drug formulation may be administered less frequently to the patient while achieving a similar or improved therapeutic effect.

The conjugates of this invention are anticipated to exhibit inhibition, in vivo, of adhesion of leukocytes to endothelial cells mediated by VLA-4 by competitive binding to VLA-4. Preferably, the compounds of this invention can be used in intravenous formulations for the treatment of diseases mediated by VLA-4 or leukocyte adhesion. Such diseases include inflammatory diseases in mammalian patients such as asthma, Alzheimer's disease, atherosclerosis, AIDS dementia, diabetes (including acute juvenile onset diabetes), inflammatory bowel disease (including ulcerative colitis and Crohn's disease), multiple sclerosis, rheumatoid arthritis, tissue transplantation, tumor metastasis, meningitis, encephalitis, stroke, and other cerebral traumas, nephritis, retinitis, atopic dermatitis, psoriasis, myocardial ischemia and acute leukocyte-mediated lung injury such as that which occurs in adult respiratory distress syndrome. The formulations of the present invention are especially useful in the treatment of multiple sclerosis and rheumatoid arthritis.

Appropriate in vivo models for demonstrating efficacy in treating inflammatory conditions include EAE (experimental autoimmune encephalomyelitis) in mice, rats, guinea pigs or primates, as well as other inflammatory models dependent upon α4 integrins.

Inflammatory bowel disease is a collective term for two similar diseases referred to as Crohn's disease and ulcerative colitis. Crohn's disease is an idiopathic, chronic ulceroconstrictive inflammatory disease characterized by sharply delimited and typically transmural involvement of all layers of the bowel wall by a granulomatous inflammatory reaction. Any segment of the gastrointestinal tract, from the mouth to the anus, may be involved, although the disease most commonly affects the terminal ileum and/or colon. Ulcerative colitis is an inflammatory response limited largely to the colonic mucosa and submucosa. Lymphocytes and macrophages are numerous in lesions of inflammatory bowel disease and may contribute to inflammatory injury.

Asthma is a disease characterized by increased responsiveness of the tracheobronchial tree to various stimuli potentiating paroxysmal constriction of the bronchial airways. The stimuli cause release of various mediators of inflammation from IgE-coated mast cells including histamine, eosinophilic and neutrophilic chemotactic factors, leukotrines, prostaglandin and platelet activating factor. Release of these factors recruits basophils, eosinophils and neutrophils, which cause inflammatory injury.

Atherosclerosis is a disease of arteries (e.g., coronary, carotid, aorta and iliac). The basic lesion, the atheroma, consists of a raised focal plaque within the intima, having a core of lipid and a covering fibrous cap. Atheromas compromise arterial blood flow and weaken affected arteries. Myocardial and cerebral infarcts are a major consequence of this disease. Macrophages and leukocytes are recruited to atheromas and contribute to inflammatory injury.

Rheumatoid arthritis is a chronic, relapsing inflammatory disease that primarily causes impairment and destruction of joints. Rheumatoid arthritis usually first affects the small joints of the hands and feet but then may involve the wrists, elbows, ankles and knees. The arthritis results from interaction of synovial cells with leukocytes that infiltrate from the circulation into the synovial lining of the joints. See e.g., Paul, *Immunology* (3d ed., Raven Press, 1993).

Another indication for the compounds of this invention is in treatment of organ or graft rejection mediated by VLA-4. Over recent years there has been a considerable improvement in the efficiency of surgical techniques for transplanting tissues and organs such as skin, kidney, liver, heart, lung, pancreas and bone marrow. Perhaps the principal outstanding problem is the lack of satisfactory agents for inducing immunotolerance in the recipient to the transplanted allograft or organ. When allogeneic cells or organs are transplanted into a host (i.e., the donor and donee are different individuals from the same species), the host immune system is likely to mount an immune response to foreign antigens in the transplant (host-versus-graft disease) leading to destruction of the transplanted tissue. $CD^{8+}$ cells, CD4 cells and monocytes are all involved in the rejection of transplant tissues. Compounds of this invention which bind to alpha-4 integrin are useful, inter alia, to block alloantigen-induced immune responses in the donee thereby preventing such cells from participating in the destruction of the transplanted tissue or organ. See, e.g., Paul et al., *Transplant International* 9, 420-425 (1996); Georczynski et al., *Immunology* 87, 573-580 (1996); Georcyznski et al., *Transplant. Immunol.* 3, 55-61 (1995); Yang et al., *Transplantation* 60, 71-76 (1995); Anderson et al., *APMIS* 102, 23-27 (1994).

A related use for compounds of this invention which bind to VLA-4 is in modulating the immune response involved in "graft versus host" disease (GVHD). See e.g., Schlegel et al., *J. Immunol.* 155, 3856-3865 (1995). GVHD is a potentially fatal disease that occurs when immunologically competent cells are transferred to an allogeneic recipient. In this situation, the donor's immunocompetent cells may attack tissues in the recipient. Tissues of the skin, gut epithelia and liver are frequent targets and may be destroyed during the course of GVHD. The disease presents an especially severe problem when immune tissue is being transplanted, such as in bone marrow transplantation; but less severe GVHD has also been reported in other cases as well, including heart and liver transplants. The therapeutic agents of the present invention are used, inter alia, to block activation of the donor T-cells thereby interfering with their ability to lyse target cells in the host.

A further use of the compounds of this invention is inhibiting tumor metastasis. Several tumor cells have been reported to express VLA-4 and compounds which bind VLA-4 block adhesion of such cells to endothelial cells. Steinback et al., *Urol. Res.* 23, 175-83 (1995); Orosz et al., *Int. J. Cancer* 60, 867-71 (1995); Freedman et al., *Leuk. Lymphoma* 13, 47-52 (1994); Okahara et al., *Cancer Res.* 54, 3233-6 (1994).

Compounds having the desired biological activity may be modified as necessary to provide desired properties such as improved pharmacological properties (e.g., in vivo stability, bio-availability), or the ability to be detected in diagnostic applications. Stability can be assayed in a variety of ways such as by measuring the half-life of the proteins during incubation with peptidases or human plasma or serum. A number of such protein stability assays have been described (see, e.g., Verhoef et al., Eur. J. Drug Metab. Pharmacokinet., 1990, 15(2):83-93).

A further use of the compounds of this invention is in treating multiple sclerosis. Multiple sclerosis is a progressive neurological autoimmune disease that affects an estimated 250,000 to 350,000 people in the United States. Multiple sclerosis is thought to be the result of a specific autoimmune reaction in which certain leukocytes attack and initiate the destruction of myelin, the insulating sheath covering nerve fibers. In an animal model for multiple sclerosis, murine monoclonal antibodies directed against VLA-4 have been shown to block the adhesion of leukocytes to the endothelium, and thus prevent inflammation of the central nervous system and subsequent paralysis in the animals.[16]

Pharmaceutical compositions of the invention are suitable for use in a variety of drug delivery systems. Suitable formulations for use in the present invention are found in *Remington's Pharmaceutical Sciences*, Mace Publishing Company, Philadelphia, Pa., 17th ed. (1985).

The amount administered to the patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the symptoms of the disease and its complications. An amount adequate to accomplish this is defined as "therapeutically effective dose." Amounts effective for this use will depend on the disease condition being treated as well as by the judgment of the attending clinician depending upon factors such as the severity of the inflammation, the age, weight and general condition of the patient, and the like, with reference to the appropriate animal model data, such as that provided herein. Methods for estimating appropriate human dosages, based on such data, are known in the art. (see, for example, Wagner, J.G. Pharmacokinetics for the Pharmaceutical Scientist. Technomic, Inc., Lancaster, Pa. 1993).

The compositions administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration.

The therapeutic dosage of the compounds of the present invention will vary according to, for example, the particular use for which the treatment is made, the manner of administration of the compound, the health and condition of the patient, and the judgment of the prescribing physician. For example, for intravenous administration, the dose will typically be in the range of about 20 µg to about 2000 µg per kilogram body weight, preferably about 20 µg to about 500 µg, more preferably about 100 µg to about 300 µg per kilogram body weight. Suitable dosage ranges for intranasal administration are generally about 0.1 pg to 1 mg per kilogram body weight. Effective doses can be extrapolated from dose-response curves derived from in vitro or animal model test systems.

Compounds of this invention are also capable of binding or antagonizing the actions of $\alpha_6\beta_1$, $\beta_9\beta_1$, $\alpha_4\beta_7$, $\alpha_d\beta_2$, $\alpha_e\beta_7$ integrins (although $\alpha_4\beta_1$ and $\alpha_9\beta_1$ are preferred in this invention). Accordingly, compounds of this invention are also useful for preventing or reversing the symptoms, disorders or diseases induced by the binding of these integrins to their respective ligands.

For example, International Publication Number WO 98/53817, published Dec. 3, 1998 (the disclosure of which is incorporated herein by reference in its entirety) and references cited therein describe disorders mediated by $\alpha_4\beta_7$. This reference also describes an assay for determining antagonism of $\alpha_4\beta_7$ dependent binding to VCAM-Ig fusion protein.

Additionally, compounds that bind $\alpha_d\beta_2$ and $\alpha_e\beta_7$ integrins are particularly useful for the treatment of asthma and related lung diseases. See, for example, M. H. Grayson et al., *J. Exp. Med.* 1998, 188(11) 2187-2191. Compounds that bind $\alpha_e\beta_7$ integrin are also useful for the treatment of systemic lupus erythematosus (see, for example, M. Pang et al., *Arthritis Rheum.* 1998, 41(8), 1456-1463); Crohn's disease, ulcerative colitis and inflammatory bowel disease (IBD) (see, for example, D. Elewaut et al., *Scand J. Gastroenterol* 1998, 33(7) 743-748); Sjogren's syndrome (see, for example, U. Kroneld et al., *Scand J. Gastroenterol* 1998, 27(3), 215-218); and rheumatoid arthritis (see, for example, *Scand J. Gastroenterol* 1996, 44(3), 293-298). And compounds that bind $\alpha_6\beta_1$ may be useful in preventing fertilization (see, for example, H. Chen et al., *Chem. Biol.* 1999, 6, 1-10).

In another aspect of the invention, the compounds and compositions described herein can be used to inhibit immune cell migration from the bloodstream to the central nervous system in the instance of, for example, multiple sclerosis, or to areas which result in inflammatory-induced destruction of the myelin. Preferably, these reagents inhibit immune cell migration in a manner that inhibits demyelination and that further may promote remyelination. The reagents may also prevent demyelination and promote remyelination of the central nervous system for congenital metabolic disorders in which infiltrating immune cells affect the development myelin sheath, mainly in the CNS. The reagents preferably also reduce paralysis when administered to a subject with paralysis induced by a demyelinating disease or condition.

Inflammatory diseases that are included for treatment by the compositions, compounds and methods disclosed herein include generally conditions relating to demyelination. Histologically, myelin abnormalities are either demyelinating or dysmyelinating. Demyelination implies the destruction of myelin. Dysmyelination refers to defective formation or maintenance of myelin resulting from dysfunction of the oligodendrocytes. Preferably, the compositions and methods disclosed herein are contemplated to treat diseases and conditions relating to demyelination and aid with remyelination. Additional diseases or conditions contemplated for treatment include meningitis, encephalitis, and spinal cord injuries and conditions generally which induce demyelination as a result of an inflammatory response.

The compositions, compounds and cocktails disclosed herein are contemplated for use in treating conditions and diseases associated with demyelination. Diseases and conditions involving demyelination include, but are not limited to, multiple sclerosis, congenital metabolic disorders (e.g., phenylketonuria, Tay-Sachs disease, Niemann-Pick disease, Gaucher's disease, Hurler's syndrome, Krabbe's disease and other leukodystrophies), neuropathies with abnormal myelination (e.g., Guillain Barre, chronic immune demyelinating polyneuropathy (CIDP), multifocal CIDP, anti-MAG syndrome, GALOP syndrome, anti-sulfatide antibody syndrome, anti-GM2 antibody syndrome, POEMS syndrome, perineuritis, IgM anti-GD 1b antibody syndrome), drug related demyelination (e.g., caused by the administration of chloroquine, FK506, perhexiline, procainamide, and zimeldine), other hereditary demyelinating conditions (e.g., carbohydrate-deficient glycoprotein, Cockayne's syndrome, congenital hypomyelinating, congenital muscular dystrophy, Farber's disease, Marinesco-Sjögren syndrome, metachromatic leukodystrophy, Pelizaeus-Merzbacher disease, Refsum disease, prion related conditions, and Salla disease) and other demyelinating conditions (e.g., meningitis, encephalitis or spinal cord injury) or diseases.

There are various disease models that can be used to study these diseases in vivo. For example, animal models include but are not limited to:

TABLE 4

| Disease Model | Species |
| --- | --- |
| EAE | Mouse, rat, guinea pig |
| Myelin-oligodendrocyte glycoprotein (MOG) induced EAE | Rat |
| TNF-α transgenic model of demyelination | Mouse |

Multiple Sclerosis

The most common demyelinating disease is multiple sclerosis, but many other metabolic and inflammatory disorders result in deficient or abnormal myelination. MS is a chronic neurologic disease, which appears in early adulthood and progresses to a significant disability in most cases. There are approximately 350,000 cases of MS in the United States alone. Outside of trauma, MS is the most frequent cause of neurologic disability in early to middle adulthood.

The cause of MS is yet to be determined. MS is characterized by chronic inflammation, demyelination and gliosis (scarring). Demyelination may result in either negative or positive effects on axonal conduction. Positive conduction abnormalities include slowed axonal conduction, variable conduction block that occurs in the presence of high-but not low-frequency trains of impulses or complete conduction block. Positive conduction abnormalities include ectopic impulse generation, spontaneously or following mechanical stress and abnormal "cross-talk" between demyelinated exons.

T cells reactive against myelin proteins, either myelin basic protein (MBP) or myelin proteolipid protein (PLP) have been observed to mediate CNS inflammation in experimental allergic encephalomyelitis. Patients have also been observed as having elevated levels of CNS immunoglobulin (Ig). It is further possible that some of the tissue damage observed in MS is mediated by cytokine products of activated T cells, macrophages or astrocytes.

Today, 80% patients diagnosed with MS live 20 years after onset of illness. Therapies for managing MS include: (1) treatment aimed at modification of the disease course, including treatment of acute exacerbation and directed to long-term suppression of the disease; (2) treatment of the symptoms of MS; (3) prevention and treatment of medical complications; and (4) management of secondary personal and social problems.

The onset of MS may be dramatic or so mild as to not cause a patient to seek medical attention. The most common symptoms include weakness in one or more limbs, visual blurring due to optic neuritis, sensory disturbances, diplopia and ataxia. The course of disease may be stratified into three general categories: (1) relapsing MS, (2) chronic progressive MS, and (3) inactive MS. Relapsing MS is characterized by recurrent attacks of neurologic dysfunction. MS attacks generally evolve over days to weeks and may be followed by complete, partial or no recovery. Recovery from attacks generally occurs within weeks to several months from the peak of symptoms, although rarely some recovery may continue for 2 or more years.

Chronic progressive MS results in gradually progressive worsening without periods of stabilization or remission. This form develops in patients with a prior history of relapsing MS, although in 20% of patients, no relapses can be recalled. Acute relapses also may occur during the progressive course.

A third form is inactive MS. Inactive MS is characterized by fixed neurologic deficits of variable magnitude. Most patients with inactive MS have an earlier history of relapsing MS.

Disease course is also dependent on the age of the patient. For example, favourable prognostic factors include early onset (excluding childhood), a relapsing course and little residual disability 5 years after onset. By contrast, poor prognosis is associated with a late age of onset (i.e., age 40 or older) and a progressive course. These variables are interdependent, since chronic progressive MS tends to begin at a later age that relapsing MS. Disability from chronic progressive MS is usually due to progressive paraplegia or quadriplegia (paralysis) in patients. In one aspect of the invention, patients will preferably be treated when the patient is in remission rather then in a relapsing stage of the disease.

Short-term use of either adrenocorticotropic hormone or oral corticosteroids (e.g., oral prednisone or intravenous methylprednisolone) is the only specific therapeutic measure for treating patients with acute exacerbation of MS.

Newer therapies for MS include treating the patient with interferon beta-lb, interferon beta-1a, and Copaxone® (formerly known as copolymer 1). These three drugs have been shown to significantly reduce the relapse rate of the disease. These drugs are self-administered intramuscularly or subcutaneously.

However, none of the current treatment modalities inhibit demyelination, let alone promotes or allows spontaneous remyelination or reduces paralysis. One aspect of the invention contemplates treating MS with agents disclosed herein either alone or in combination with other standard treatment modalities.

Congenital Metabolic Disorders

Congenital metabolic disorders include phenylketonuria (PKU) and other aminoacidurias, Tay-Sachs disease, Niemann-Pick disease, Gaucher's disease, Hurler's syndrome, Krabbe's disease and other leukodystrophies that impact the developing sheath as described more fully below.

PKU is an inherited error of metabolism caused by a deficiency in the enzyme phenylalanine hydroxylase. Loss of this enzyme results in mental retardation, organ damage, unusual posture and can, in cases of maternal PKU, severely compromise pregnancy. A model for studying PKU has been discovered in mice. Preferably infants identified with PKU are sustained on a phenylalanine free or lowered diet. An aspect of the invention would be to combine such diets with the compounds and compositions disclosed herein to prevent demyelination and remyelinate cells damaged due to PKU.

Classical Tay-Sachs disease appears in the subject at about age 6 months and will eventually result in the death of the subject by age 5 years. The disease is due to the lack of the enzyme, hexoaminidase A (hex A), which is necessary for degrading certain fatty substances in the brain and nerve cells. The substances in the absence of the enzyme accumulate and lead to the destruction of nerve cells. Another form of hex A enzyme deficiency occurs later in life and is referred to as juvenile, chronic and adult onset forms of hex A deficiency. Symptoms are similar to those that characterize classical Tay-Sachs disease. There is also an adult onset form of the enzyme deficiency. Currently there is no cure or treatment for the disease/deficiency, only the preventative measure of in utero testing of the fetus for the disease. Thus, the compounds and compositions disclosed herein may be useful in ameliorating or preventing the destruction of nerve cells in such patients.

Niemann-Pick disease falls into three categories: the acute infantile form, Type B is a less common, chronic, non-neurological form, and Type C is a biochemically and genetically distinct form of the disease. In a normal individual, cellular cholesterol is imported into lysosomes for processing, after which it is released. Cells taken from subjects with Niemann-Pick have been shown to be defective in releasing cholesterol from lysosomes. This leads to an excessive build-up of cholesterol inside lysosomes, causing processing errors. NPC1 was found to have known sterol-sensing regions similar to those in other proteins, which suggests it plays a role in regulating cholesterol traffic. No successful therapies have been identified for Types A and C forms of Neumann-Pick. For Type C, patients are recommended to follow a low-cholesterol diet. Thus, the compounds and compositions disclosed herein may be useful in ameliorating or preventing the destruction of the cells.

Gaucher's disease is an inherited illness caused by a gene mutation. Normally, this gene is responsible for an enzyme called glucocerebrosidase that the body needs to break down the fat, glucocerebroside. In patients with Gaucher's disease, the body is not able to properly produce this enzyme and the fat cannot be broken down. Like Tay-Sachs disease, Gaucher's disease is considerably more common in the descendants of Jewish people from Eastern Europe (Ashkenazi), although individuals from any ethnic group may be affected. Among the Ashkenazi Jewish population, Gaucher's disease is the most common genetic disorder, with an incidence of approximately 1 in 450 persons. In the general public, Gaucher's disease affects approximately 1 in 100,000 persons.

In 1991, enzyme replacement therapy became available as the first effective treatment for Gaucher's disease. The treatment consists of a modified form of the glucocerebrosidase enzyme given intravenously. It is contemplated that the compositions and compounds disclosed herein can be used alone or more preferably in combination with glycocerebrosidase administration to treat the disease in an afflicted subject.

Hurler's syndrome, also known as mucopolysaccharidosis type I, is a class of overlapping diseases. These genetic diseases share in common the cellular accumulation of mucopolysaccharides in fibroblasts. The diseases are genetically distinguishable. Fibroblast and bone marrow transplantation does not seem to be helpful, thus compounds and compositions useful in ameliorating disease severity and progression are needed. The compounds and compositions disclosed herein may be administered to a subject to ameliorate disease progression and/or severity.

Krabbe's disease (also known as Globoid cell leukodystrophy) is an autosomal recessive condition resulting from galactosylceramidase (or galactocerebrosidase) deficiency, a lysosomal enzyme that catabolises a major lipid component of myelin. Incidence in France is an estimated 1:150,000 births. The disease leads to demyelination of the central and peripheral nervous system. Onset generally occurs during the first year of life and the condition is rapidly progressive, but juvenile, adolescent or adult onset forms have also been reported, with a more variable rate of progression. Diagnosis is established from enzyme assay (galactosylceramidase deficiency). There are several natural animal models (mouse, dog, monkey). Krabbe's disease, like all leukodystrophies, has no known cures or effective treatments. One embodiment of the instant invention is to use the compositions and compounds disclosed herein to treat or ameliorate Krabbe's disease and other leukodystrophies.

Leukodystrophies are a group of genetically determined progressive disorders that affect the brain, spinal cord and peripheral nerves. They include adrenoleukodystrophy (ALD), adrenomyeloneuropathy (AMN), Aicardi-Goutiers syndrome, Alexander's disease, CACH (i.e., childhood ataxia with central nervous system hypomyelination or vanishing white matter disease), CADASIL (i.e., cerebral autosomal dominant arteriopathy with subcortical infarcts and leukoencephalopathy), Canavan disease (spongy degeneration), Cerebrotendinous Xanthomatosis (CTX), Krabbe's disease (discussed above), metachromatic leukodystrophy (MLD), neonatal adrenoleukodystrophy, ovarioleukodystrophy syndrome, Pelizaeus-Merzbacher disease (X-linked spastic paraglegia), Refsum disease, van der Knaap syndrome (vaculating leukodystrophy with subcortical cysts) and Zellweger syndrome. None of the diseases have effective treatments let alone cures. Consequently, means of treating or ameliorating the symptoms of the disease, such as by using the compositions and compounds disclosed herein, is needed.

Neuropathies with Abnormal Myelination

A variety of chronic immune polyneuropathies exist which result in demyelination in the patient. The age of onset for the conditions varies by condition. Standard treatments for these diseases exist and could be combined with the compositions and compounds disclosed herein. Alternatively, the compositions and compounds disclosed can be used alone. Existing standard therapies include the following:

TABLE 5

| Neuropathy | Clinical Features | Treatment |
|---|---|---|
| Chronic Immune Demyelinating Polyneuropathy (CIDP) | Onset between 1-80 years. Characterized by weakness, sensory loss, and nerve hypertrophy. | T-cell immunosuppression with prednisone, cyclosporine A or methotrexate, HIG, plasma exchange |
| Multifocal CIDP | Onset between 28 to 58 years and characterized by asymmetric weakness, sensory loss with a course that is slowly progressive or relapsing-remitting. | T cell immunosuppression with prednisone Human immunoglobulin (HIG) |
| Multifocal Motor Neuropathy (MMN) | Onset ranges from 25 to 70 years, with twice as many men as women. Features include weakness, muscle atrophy, fasciculations, and cramps which are progressive over 1-30 years. | HIG B cell immunosuppression with plasma exchange cyclophosphamide, Rituxan |
| Neuropathy with IgM binding to Myelin-Associated Glycoprotein (MAG) | Onset is usually over age 50 and is characterized by sensory loss (100%), weakness, gain disorder, tremor which is all slowly progressive. | B-cell immunosuppression plasma exchange cyclophosphamide Rituxan α-interferon cladribine or fludarabine prednisone |
| GALOP Syndrome (Gait disorder, Autoantibody, Late-age, Onset, Polyneuropathy) | A gait disorder with polyneuropathy | HIG Plasma exchange cyclophosphamide |
| POEMS Syndrome (Polyneuropathy, Organomegaly, Endocrinopathy, M-Protein and Skin changes) also known as Crow-Fukase Syndrome and Takatsuki disease | Onset occurs between 27 and 80 years with weakness, sensory loss, reduced or absent tendon reflexes, skin disorders and other features. | Osteosclerotic lesions are treated with irradiation. Widespread lesions with chemotherapy (Melphalan and prednisone). |

Drug and Radiation Induced Demyelination

Certain drugs and radiation can induce demyelination in subjects. Drugs that are responsible for demyelination include but are not limited to chloroquine, FK506, perhexiline, procainamide, and zimeldine.

Radiation also can induce demyelination. Central nervous system (CNS) toxicity due to radiation is believed to be cause by (1) damage to vessel structures, (2) deletion of oligodendrocyte-2 astrocyte progenitors and mature oligodendrocytes, (3) deletion of neural stem cell populations in the hippocampus, cerebellum and cortex, and generalized alterations of cytokine expression. Most radiation damage results from radiotherapies administered during the treatment of certain cancers. See for review Belka et al., 2001 *Br. J. Cancer* 85: 1233-9. However, radiation exposure may also be an issue for astronauts (Hopewell, 1994 *Adv. Space Res.* 14: 433-42) as well as in the event of exposure to radioactive substances.

Patients who have received drugs or been exposed accidentally or intentionally to radiation may experience a benefit by administered one of the compounds or compositions disclosed herein to prevent demyelination or to promote remyelination.

Conditions Involving Demyelination

Additional inherited syndromes/diseases that result in demyelination include Cockayne's syndrome, congenital hypomyelinating, Farber's disease, metachromatic leukodystrophy, Peliszaeus-Merzbacher disease, Refsum, prion related conditions and Salla disease.

Cockayne's syndrome (CS) is a rare inherited disorder in which people are sensitive to sunlight, have short stature and have the appearance of premature aging. In the classical form of Cockayne's syndrome (Type I), the symptoms are progressive and typically become apparent after the age of one year. An early onset or congenital form of Cockayne's syndrome (Type II) is apparent at birth. Interestingly, unlike other DNA repair diseases, Cockayne's syndrome is not linked to cancer. CS is a multi-system disorder that causes both profound growth failure of the soma and brain and progressive cachexia, retinal, cochlear, and neurologic degeneration, with a leukodystrophy and demyelinating neuropathy without an increase in cancer. After exposure to UV (e.g., sunlight), subjects with Cockayne's syndrome can no longer perform transcription-coupled repair. Two genes defective in Cockayne's syndrome, CSA and CSB, have been identified so far. The CSA gene is found on chromosome 5. Both genes code for proteins that interacts with components of the transcriptional machinery and with DNA repair proteins.

To date, no cures or effective treatments for patients with this disease have been identified. Thus, one aspect of the invention is treatment of this disease with the compounds and compositions disclosed herein.

Congenital hypomyelination has several names including congenital dysmyelinating neuropathy, congenital hypomyelinating polyneuropathy, congenital hypomyelination (Onion Bulb) polyneuropathy, congenital hypomyelination neuropathy, congenital neuropathy caused by hypomyelination, hypomyelination neuropathy and CHN. Hereditary peripheral neuropathies, among the most common genetic disorders in humans, are a complex, clinically and genetically heterogeneous group of disorders that produce progressive deterioration of the peripheral nerves. Congenital hypomyelination is one of a group of disorders. This group includes hereditary neuropathy with liability to pressure palsies, Charcot-Marie-Tooth disease, Dejerine-Sottas syndrome, and congenital hypomyelinating neuropathy. There are no known cures or effective treatments for any of these disorders.

Farber's disease has several names including: Farber lipogranulomatosis, ceremidase deficiency, acid ceramidase deficiency, AC deficiency, N-laurylsphingosine deacylase deficiency, and N-acylsphingosine amidohydrolase. As certain names reveal, the disease occurs due to a deficiency of acid ceramidase (also known as N-acylsphingosine amidohydrolase, ASAH). The lack of the enzyme results in an accumulation of non-sulfonated acid mucopolysaccharide in the neurons and glial cells. Patients with the disease usually die before the age of 2 years.

Metachromatic leukodystrophy (MLD) is a genetic disorder caused by a deficiency of the enzyme arylsulfatase A. It is one of a group of genetic disorders called the leukodystrophies that affect growth of the myelin sheath. There are three forms of MLD: late infantile, juvenile, and adult. In the late infantile form, which is the most common, onset of symptoms begins between ages 6 months and 2 years. The infant is usually normal at birth, but eventually loses previously gained abilities. Symptoms include hypotonia (low muscle tone), speech abnormalities, loss of mental abilities, blindness, rigidity (i.e., uncontrolled muscle tightness), convulsions, impaired swallowing, paralysis, and dementia. Symptoms of the juvenile form begin between ages 4 and 14, and include impaired school performance, mental deterioration, ataxia, seizures, and dementia. In the adult form, symptoms, which begin after age 16, may include impaired concentration, depression, psychiatric disturbances, ataxia, tremor, and dementia. Seizures may occur in the adult form, but are less common than in the other forms. In all three forms mental deterioration is usually the first sign.

Peliszaeus-Merzbacher disease (also known as perinatal sudanophilic leukodystrophy) is an X-linked genetic disorder that causes an abnormality of a proteolipid protein. The abnormality results in an infant's death typically before the age of one year. There are no known treatments or cures for the disease.

Refsum disease (also referred to as phytanic acid oxidase deficiency, heredopathia atactica polyneuritiformis or hereditary motor and sensory neuropathy IV, HMSN IV) is caused by mutations in the gene, which encodes phytanoyl-CoA hydroxylase (PAHX or PHYF). The major clinical features are retinitis pigmentosa, chronic polyneuropathy and cerebellar signs. Phytanic acid, an unusual branched chain fatty acid (3,7,11,15-tetramethyl-hexadecanoic acid) accumulates in the tissues and body fluids of patients with the disease and is unable to be metabolised due to the lack of PAHX. Plasmapheresis performed once or twice monthly effectively removes the acid from the body and permits liberalization of dietary restrictions limiting phytanic acid intake.

Prion related conditions include Gerstmann-Straussler disease (GSD), Creutzfeldt-Jakob disease (CJD), familial fatal insomnia and aberrant isoforms of the prion protein can act as infectious agents in these disorders as well as in kuru and scrapie (a disease found in sheep). The term prion derives from "protein infectious agent" (Prusiner, *Science* 216: 136-44, 1982). There is a proteolytic cleavage of the prion related protein (PRP) which results in an amyloidogenic peptide that polymerises into insoluble fibrils.

Salla disease and other types of sialurias are diseases involving problems with sialic acid storage. They are autosomal recessive neurodegenerative disorders that may present as a severe infantile form (i.e., ISSD) or as a slowly progressive adult form that is prevalent in Finland (i.e., Salla disease). The main symptoms are hypotonia, cerebellar ataxia and mental retardation. These conditions and diseases are also contemplated for palliative or ameliorating treatments.

Other conditions that result in demyelination include postinfectious encephalitis (also known as acute disseminated encephalomyelitis, ADEM), meningitis and injuries to the spinal cord. The compositions and compounds disclosed herein are also contemplated for use in treating these other demyelinating conditions.

The following synthetic and biological examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning.

Å=Angstroms
br s=broad singlet
BSA=bovine serum albumin
d=doublet
dd=doublet of doublets
dq=doubet of quartets
dsextet=doublte of sextets
DMF=dimethylformamide
EDTA=ethylenediamine tetraacetic acid
EtOAc=ethyl acetate
EM=wavelength of emission (in nm)
EX=wavelength of excitation (in nm)
g=gram
HBSS=Hank's balanced salt solution
HEPES=4-(2-hydroxyethyl)-1-piperazineethanesulfonic acid
HPLC=high performance liquid chromatography hrs or h=hours
in.=inch
i-PrOH=iso-propanol
kg=kilogram
L=liters
LC/MS=liquid chromatography/mass spectroscopy
$m^2$=multiplet
m=square meters
M=molar
mbar=millibar
mg=milligram
MHz=megahertz
min.=minutes
mL=milliliters
mm=millimeters
mM=millimolar
mmol=millimoles
mOsm=milliosmol
m/z=mass to charge ratio
N=normal
ng=nanograms
nm=nanometers
NMR=nuclear magnetic resonance
PBS=phosphate buffered saline
PBS++=PBS with calcium and magnesium
ppm=parts per million
psi=pounds per square inch
q=quartet
Rf=retention factor (ratio of distance traveled by substance/distance traveled by solvent front)
rpm=rotations per minute
rt=room temperature
s=singlet
t=triplet
TFA=trifluoroacetic acid
THF=tetrahydrofuran
TLC=thin layer chromatography
UV=ultraviolet
wt/wt=weight to weight ratio
w/v=weight to volume ratio
µg=micrograms
µm=microns
µM=micromolar General Methods. Flash chromatography was performed using a biotage Flash 75L, using 800 g KP-Sil silica cartridges (32-63 µM, 60 Å, 500-550 $m^2$/g). Rf's are reported for analytical TLC, using EM Sciences Silica Gel 60 F(254), 250 µM thick plates for normal phase. NMR spectra were obtained on a Varian Gemini 300 MHz spectrometer (300 MHz for $^1$H spectra and 75 MHz for $^{13}$C spectra). Analytical HPLC was performed on an Agilent 1100 Series HPLC with a Phenomenex Luna, 3 µm, C-1 8, 30×4.6 mm column. The detector was UV at 210 nm. Solvents were 0.1% TFA in water and 0.1% TFA in acetonitrile. The standard flow rate was 1.5 mL/min., and in the standard method the solvent gradient changed from 20% $CH_3CN$ to 70% $CH_3CN$ over 2.33 minutes. A second alternative method has a flow rate of 2 mL/min. and a gradient changing from 20% $CH_3CN$ to 70% $CH_3CN$ over 1.75 minutes. A third method has a flow rate of 1.5 ml/min. with the solvent composition changing from 20% $CH_3CN$ to 70% $CH_3CN$ over 10 min., holding at 70% for 2 min., then ramping to 95% over 1 min. and holding at 95% for 2 minutes. LC/MS was performed on an Agilent 1100 Series HPLC with a Series 1100 MSD with electrospray ionization (unless otherwise indicated as chemical ionization). The column and conditions were matched to the free standing HPLC. $^1$H NMR of amides typically show rotamers and integration of some peaks are reported in fractional proton values.

Example 1

Preparation of N-[2-diethylamino-5-{N-ethyl-N-(furan-3-ylcarbonyl)amino}pyrimidin-4-yl]-L-4'-{(pyrrolidin-1-yl)carbonyloxy}phenylalanine

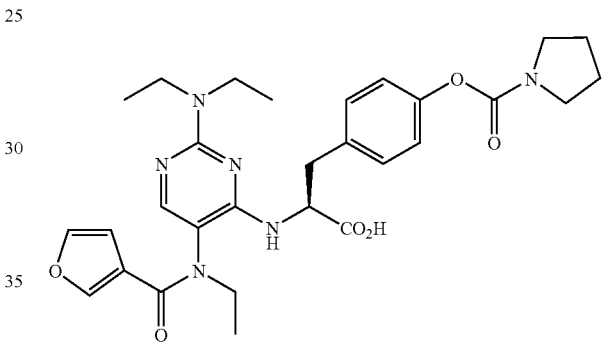

Step 1: Preparation of N-[2-diethylamino-5-{N-amino}pyrimidin-4-yl]-L-4'-{(pyrrolidin-1-yl)carbonyloxy}phenylalanine tert-butyl ester 2

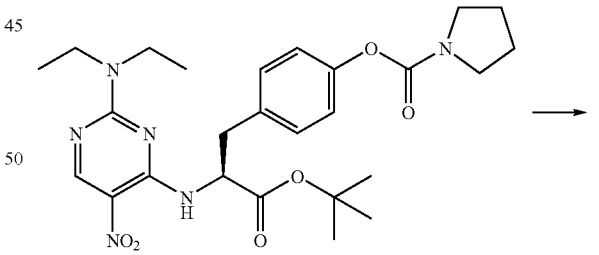

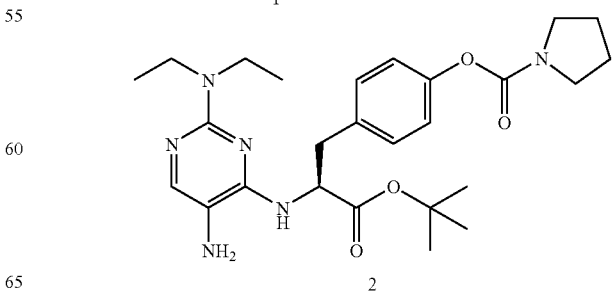

A mixture of nitropyrimidine-carbamate 1 (160.25 g, 0.3035 mol; prepared as in WO 03/099809) and 5% Pd/C (15 g, 50/50 wt/wt with H₂O, Degussa E 101 R/W) in THF-water solution (1 L THF and 50 mL H₂O) was stirred under 60 psi hydrogen at rt. After 22 hrs, TLC (50% EtOAc/hexanes on silica gel) showed 100% conversion to product. The reaction mixture was filtered through a Celite pad (200 mL). The hydrogenation flask and the celite pad were rinsed with fresh, anhydrous THF (500 mL) to give a green filtrate solution. The filtrate was concentrated in vacuo to give the crude product as a greenish-black gummy oil. The rotatory evaporator was vented under N₂ and fresh, anhydrous THF (600 mL) was added. The solution was concentrated in vacuo and vented under nitrogen. (The process of dissolving in fresh, anhydrous THF and concentrating was repeated twice more to azeotropically remove residual water.) This material is used immediately in Step 2 due to apparent air sensitivity. m/z=499.5 for [M+1]⁺ for the desired product.

Step 2: Preparation of N-[2-diethylamino-5-{N-trifluoroacetylamino}pyrimidin-4-yl]-L-4'-{(pyrrolidin-1-yl)carbonyloxy}phenylalanine tert-butyl ester 3

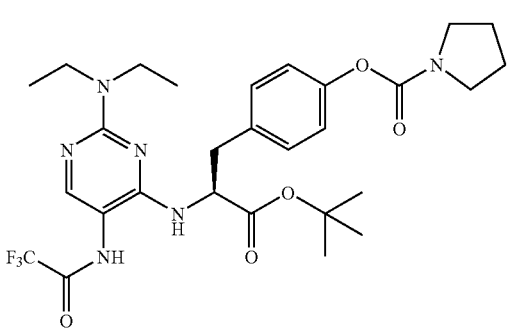

The crude aminopyrimidine carbamate 2 from Step 1 was dissolved in 600 mL anhydrous THF. The solution was cooled to 0° C. under nitrogen. Trifluoroacetic anhydride (45.5 mL, 1.51 g/mL, 327.3 mmol) was slowly added to the cold amine solution via syringe pump over 45 minutes. The solution was allowed to warm to room temperature and stirred overnight. TLC (40% EtOAc in Hexanes, silica gel) indicated the reaction was essentially complete. LC/MS analysis confirmed reaction and did not show any starting material. The reaction was diluted with ethyl acetate (1.4 L) and was washed with a mixture of water (400 mL) and saturated, aqueous NaHCO₃ (700 mL, 0° C.). The organic solution was washed with brine (700 mL) and dried over MgSO₄ (105 g) to give a tan-brown solution. The dried solution was filtered through a pad of silica gel (400 mL) to give a greenish-grey solution. (The tan colored impurity was retained on the silica gel.) The silica gel was rinsed with EtOAc (400 mL). The filtrate solution was concentrated in vacuo and the flask was vented under nitrogen to minimize exposure to oxygen. Anhydrous toluene (600 mL) was added. The solution was concentrated in vacuo and was azeotroped a second time from anhydrous toluene (400 mL) to give a green-black gummy oil. The flask was vented under N₂. This crude product m/z=595.5 for [M+1]⁺ was carried forward to Step 3.

Step 3: Preparation of N-[2-diethylamino-5-{N-ethyl-N-trifluoroacetylamino}pyrimidin-4-yl]-L-4'-{(pyrrolidin-1-yl)carbonyloxy} phenylalanine tert-butyl ester 4

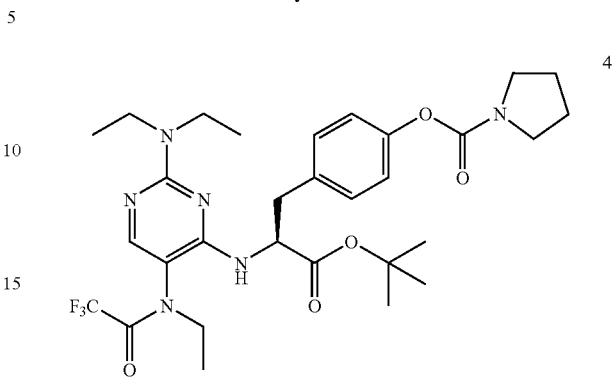

Crude trifluoroacetamidopyrimidine carbamate 3 from Step 2 was dissolved in DMF (350 mL). Solid anhydrous potassium carbonate (79.6 g, 575.7 mmol; ground to a fine powder with a mortar and pestle and then was placed in a vacuum oven at 110° C. under 28 in. Hg vacuum over night) was added. Ethyl iodide (46.5 mL, 89.8 g, 575.7 mmol) was added quickly at room temperature. The reaction flask was capped tightly and the slurry was stirred vigorously. After stirring at room temperature for 20 hours, the reaction was sampled (TLC, LC/MS). The reaction was stirred for an additional 18 hours to ensure complete reaction. Again, the reaction was sampled and a mini-workup was performed whereupon TLC analysis indicated the consumption of starting material. The reaction was diluted with 2.7 L of ethyl acetate and was stirred vigorously. The slurry was filtered through Whatman #1 filter paper to remove solid K₂CO₃. The organic solution was placed in a 6 L separatory funnel. Water (2.5 L) was added and vigorously mixed. The layers were slow to separate, then brine (200 mL) was added to break the emulsion. The organic layer was washed with another 1 L of water and then 2 L of brine.

The organic layer was dried over MgSO₄ (50 g) and Na₂SO₄ (200 g). The dried organic solution was filtered through a plug of silica gel (700 mL) to obtain an olive-drab green-tan smoky colored solution. (A purple/red baseline impurity was removed.) The silica gel was rinsed with EtOAc (800 mL). The organic solution was concentrated to give an olive drab green solid (194.3 g, 103% crude). Hexane (300 mL) was added. The sides of the flask were scrapped with a metal spatula to loosen the solid product and a magnetic stir bar was added to the flask. The mixture was rotated slowly for 30 minutes to break up the solid chunks and then quickly for 30 minutes until a fine slurry resulted. The slurry was filtered through Whatman #1 filter paper and the precipitate was rinsed with hexane (1.2 L) to give a white solid (141 g, 74% yield, 92% pure by LC/MS). The filtrate was concentrated to give a green-tan gum (33.3 g), which by TLC analysis contains some desired product.

¹H NMR (CDCl₃, 300 MHz) δ, ppm: 7.80 (apparent d, 1H), 7.18 (apparent d, AA'XX', 2H), 7.03 (apparent dd, AA'XX', 2H), 5.00 (apparent d, 1H), 4.80 (apparent dq, 1H), 3.95 (apparent dsextet, 1H), 3.4-3.7 (m, 8.5H), 3.0-3.3 (m, 3H), 2.78 (sextet, 0.7H), 1.93 (AA'BB', 4H), 1.38 (apparent d, 9H), 1.24-1.05 (m, 9H). The ¹H NMR shows rotamers as is evidenced by the doubling of most peaks.

¹³C NMR (CDCl₃, 75 MHz) δ, ppm: 166.5, 166.3, 155.6, 152.7, 150.9, 146.0, 145.9, 128.7, 128.3, 125.44, 125.39, 117.18, 77.66, (72.82, 72.28, 71.97—CDCl$_3$), 50.23, 49.74, 41.72, 41.64, 40.16, 39.90, 37.28, 32.60, 32.44, 23.24, 23.17, 21.05, 20.23, 8.50, 8.47, 7.32.

Step 4: Preparation of N-[2-diethylamino-5-{N-ethylamino} pyrimidin-4-yl]-L-4'-{(pyrrolidin-1-yl)carbonyloxy}phenylalanine tert-butyl ester 5

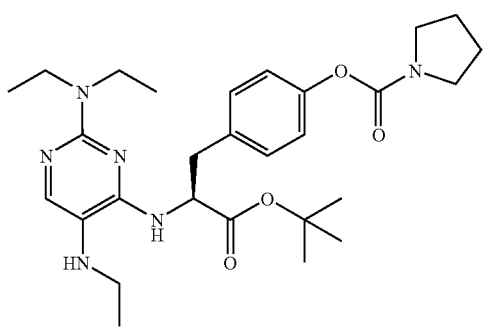

5

The trifluoroacetamide 4 (140 g) was suspended/dissolved in methanol (1.6 L). An aqueous solution of potassium carbonate (7% K$_2$CO$_3$) (480 mL) was added. (The trifluoroacetamide partially precipitated and formed a gel.) The reaction flask was lowered into a 55° C. water bath. The solution was mixed at 55° C., with monitoring by TLC, over 9 hours. The reaction was concentrated in vacuo very carefully until 1.2 L of methanol had been collected. The solution was diluted with water (200 mL) and brine (600 mL) and was extracted with EtOAc (2 L) to give an orange solution. The EtOAc layer was washed with water (1 L) and then brine (400 mL). Each of the three aqueous layers/washes was back extracted in sequential order with a single 1 L of EtOAc to obtain a bright yellow solution. The organic extracts were combined and dried over MgSO$_4$ (126 g). The dried organic solution was filtered through a pad of basic alumina (300 mL) and concentrated in vacuo to give a brown gum. After azeotroping from 600 mL toluene, a reddish solid (117.1 g) was obtained.

Step 5: Preparation of N-[2-diethylamino-5-{N-ethyl-N-(furan-3-ylcarbonyl)amino}pyrimidin-4-yl]-L-4'-{(pyrrolidin-1-yl)carbonyloxy}phenylalanine tert-butyl ester 6

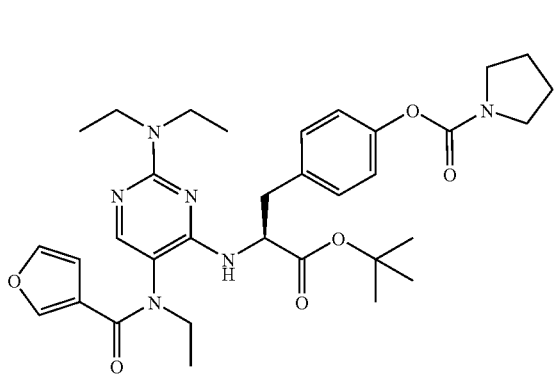

6

The amino-pyrimidine 5 (117.1 g, 222.2 mmol) was dissolved in anhydrous THF (1.5 L). Hunig's base, diisopropylethyl amine, (115 mL, 3 eq., 666.6 mmol) was added. The solution was cooled to 0° C. under N$_2$. The reaction flask was fitted with a pressure equalizing addition funnel and the addition funnel was charged with a solution of 3-furoyl chloride (32 g; Yamamoto & Maruoka; J. Am. Chem. Soc., 1981, 103, 6133-6136) in THF (90 mL). The furoyl chloride solution was added slowly to the cold amine solution over two hours. The reaction was allowed to slowly come to room temperature and was stirred for 36 hours. The reaction was diluted with EtOAc (2 L) and was washed twice with 0.2 N citric acid (1.2 L and 1.0 L), once with brine (1.8 L), and once with saturated aqueous NaHCO$_3$ (1.3 L). The bright orange-pink organic solution was dried over Na$_2$SO$_4$ (250 g) and MgSO$_4$ (51 g). The dried solution was filtered through a pad of silica gel (1 L) and the flask and silica were rinsed with EtOAc (1 L). The solution was concentrated in vacuo. During the evaporation process, a white solid crystallized. Once the solution was fully concentrated, an orange, pink, & white solid was obtained. Ether (400 mL) and hexanes (500 mL) were added. The slurry was mixed thoroughly and filtered through Whatman #1 filter paper to obtain a peach-pink solid and a bright red filtrate. The precipitate was rinsed with hexanes (500 mL), ether (800 mL), and again hexanes (400 mL) to get a light peach-orange solid. The filtrate and rinsings were combined, concentrated, and set aside for later use. The solid was dried in a vacuum oven at 60° C. for two days under a 28 in. Hg vacuum (49 Torr) to yield 100.0 g. LC/MS showed the solid to be 92% pure. The crude ester 6 was chromatographed on 2 L (1 kg) silica gel that had been slurry packed with 3 L of CH$_2$Cl$_2$. The peach colored product ester was dissolved in CH$_2$Cl$_2$ (200 mL) and was applied to the 2 L silica column. The column was eluted with CH$_2$Cl$_2$ (3 L), 50% EtOAc in hexanes (4 L), and 75% EtOAc in hexanes (4 L). Within a few minutes, desired product ester began crystallizing from several of the EtOAc-hexane fractions. Fractions that were shown to be pure by TLC were concentrated to give a white solid (82.5 g, purity >99% by LC/MS). This pure material was carried forward to the final deprotection step. Fractions that were shown by TLC to be contaminated were combined with the residue from the original filtrate/hexane & ether rinsings. This material was flash chromatographed in a manner similar to that described above to give a slight peach colored solid (13.2 g; m/z=621.5 for [M+1]$^+$).

$^1$H NMR (CDCl$_3$, 300 MHz) δ, ppm: 7.58 (apparent d, 1H), 7.35-6.90 (apparent AB overlapped with ABX, 6H), 6.45 (apparent d, 1H), 5.25 (apparent d, 1H), 4.85 (apparent dq, 1H), 4.05 (apparent octet, 1H), 3.7-3.4 (m, 8H), 3.0-3.3 (m, 2.5H), 2.90 (sextet, 0.5H), 1.93 (AA'BB', 4H), 1.38 (apparent d, 9H), 1.24-1.05 (m, 9H). The $^1$H NMR shows rotamers as is evidenced by the doubling of most peaks.

Step 6. Preparation of N-[2-diethylamino-5-{N-ethyl-N-(furan-3-ylcarbonyl)amino} pyrimidin-4-yl]-L-4'-{(pyrrolidin-1-yl)carbonyloxy}phenylalanine To the t-butyl ester 6 from Step 5 (82.5 g, 132.7 mmol) was added formic acid (2 L). The resulting solution was heated to 50° C. overnight. Analysis by TLC verified complete reaction and the solution was concentrated in vacuo. Water (~200 mL) was added to the crude product and the mixture was concentrated to dryness. Another 150 mL of water were added and the crude product was concentrated in vacuo again. The crude white solid product was concentrated from iPrOH, and twice from anhydrous THF, then dried on the rotary evaporator at 45° C. and 35-40 mbar (26-30 Torr) overnight to obtain 90 g of white solid. LC/MS showed the crude product to be 97.7% pure.

$^1$H NMR (CD$_3$OD, 300 MHz) δ, ppm: 7.65 (s, 0.55H), 7.45 (s, 0.45H), 7.38 (m, 2H), 7.25 (d, 1.3H), 7.18 (d, 1H), 7.05 (d, 1.2H), 6.90 (d, 1H), 6.55 (s, 0.55H), 6.22 (broad s, 0.45H), 4.9-4.8 residual solvent peak overlapped with sample peak, 4.10 (apparent septet, 1.11H), 3.7 (m, 3.3H), 3.58 (m, 7H), 3.45-2.9 (m, 6H), 2.78 (apparent sextet, 0.7H), 1.90 (AA'BB', 4.5H), 1.85 (m, 3.16H), 1.23-1.0 (m, 10.3H).

$^{13}$C NMR (CD$_3$OD, 75 MHz) δ, ppm: 169.6, 169.2, 160.8, 153.9, 153.6 148.8, 145.8, 145.2, 145.1, 140.7, 140.5, 138.0, 137.9, 130.3, 130.2, 124.7, 124.6, 116.5, 116.4, 116.2, 116.1, 106.9, 106.6, 105.1, 105.0, 62.4, 50.7, 50.1, 41.0, 37.9, 37.2, 30.5, 20.2, 20.0, 19.4, 6.9, 6.8, 6.1, 5.9.

Examples 2-7 below were prepared in a manner similar to example 1.

Example 2

Preparation of (S)-2-(2-(diethylamino)-5-(N-ethyl-2,2,2-trifluoroacetamido)pyrimidin-4-ylamino)-3-(4-(pyrrolidine-1-carboxyloyloxy)phenyl)propanoic acid

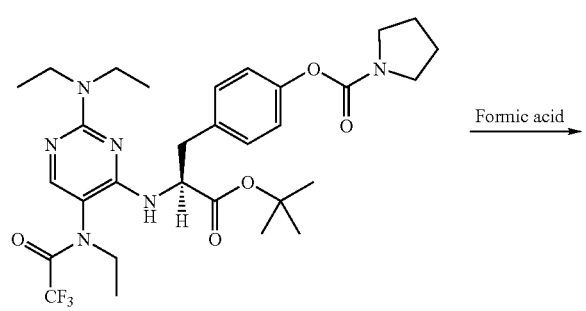

$^1$H NMR (300 MHz, CD$_3$OD) δ1.03 (1.5H, t, J=7.2 Hz), 1.10-1.28 (7.5H, m), 1.98 (4H, m), 2.67-2.85 (0.5H, m), 2.90-3.05 (0.5H, m), 3.05-3.38 (2H, m, overlap with CD$_3$OD), 3.41 (2H, m), 3.58 (6H, m), 3.90-4.11 (1H, m), 4.85-4.90 (1H, overlap with CD$_3$OD), 7.02 (2H, m), 7.26 (2H, m), 7.66 (1H, d, J=8.7 Hz)

HPLC/MS: MH$^+$=567.1

Example 3

Preparation of N-[2-diethylamino-5-{N-ethyl-N-(thien-2-ylcarbonyl)amino}pyrimidin-4-yl]-L-4'-{(pyrrolidin-1-yl)carbonyloxy}phenylalanine Step 1:

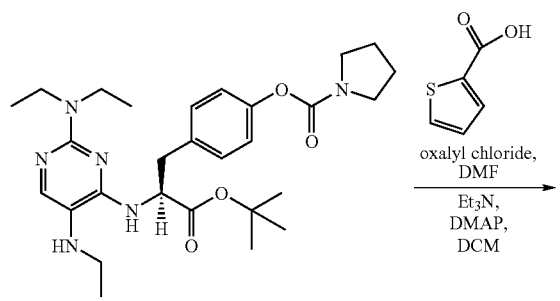

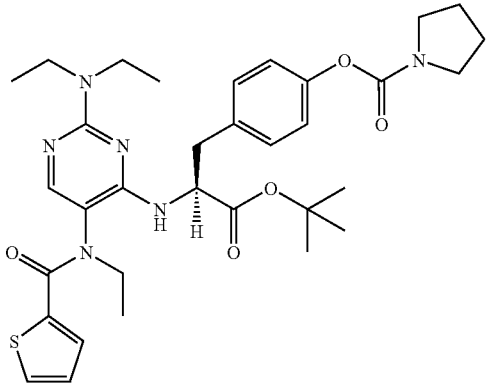

$^1$H NMR (300 MHz, CDCl$_3$) δ 1.09-1.17 (3H, m), 1.23-1.26 (3H, m), 1.47 (12H, m), 1.87-1.99 (4H, m), 2.80 (0.4H, br s), 3.10 (1.6H, m), 3.20 (1H, m), 3.44 (2H, t, J=6.0 Hz), 3.54 (2H, t, J=6.0 Hz), 3.88-4.15 (3H, m), 4.80-4.85 (1H, m), 6.48 (0.6H, br s), 6.75 (0.4H, s), 6.69-7.08 (5H, m), 7.41 (1H, s), 7.50 (1H, s), 7.78 (0.4H, br s), 7.85 (0.6H, br s) HPLC/MS: MH$^+$=637.2

Step 2:

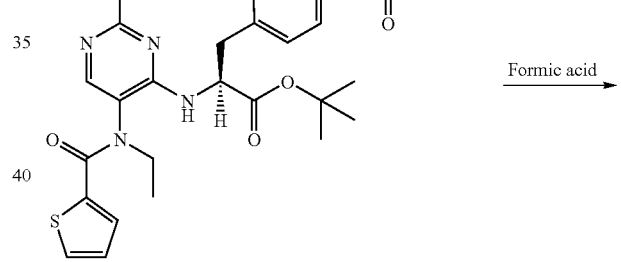

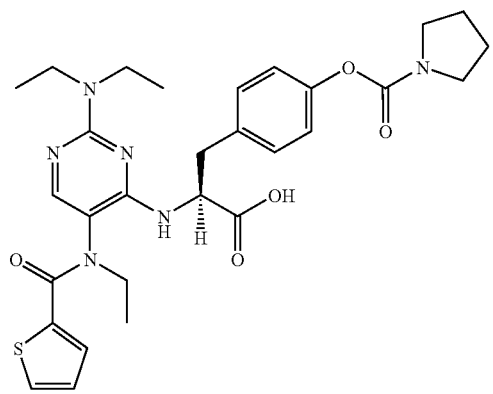

$^1$H NMR (300 MHz, CDCl$_3$) δ 0.90 (3H, t, J=6.9 Hz), 1.10-1.30 (6H, m), 1.85-1.94 (4H, m), 2.85-3.24 (2.4H, m), 3.35 (8.6H, m), 4.00-4.15 (1H, m), 4.55 (0.4H, br s), 4.73 (0.6H, br s), 5.85 (0.6H, d, J=5.7 Hz), 5.87 (0.4H, br s), 6.60-7.12 (5.4H, m), 7.39 (1H, m), 7.60-7.68 (1.6H, m)

HPLC/MS: MH$^+$=581.2

Example 4

Preparation of N-[2-diethylamino-5-{N-ethyl-N-(thien-3-ylcarbonyl)amino}pyrimidin-4-yl]-L-4'-{(pyrrolidin-1-yl)carbonyloxy}phenylalanine Step 1:

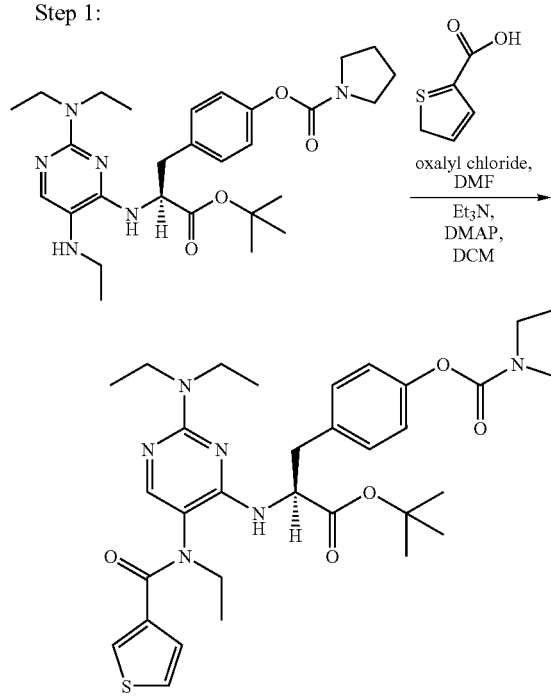

¹H NMR (300 MHz, CDCl₃) δ 1.07-1.27 (9H, m), 1.40 (9H, s), 1.90 (4H, m), 3.05-3.24 (3H, m), 3.43-3.64 (8H, m), 4.73-4.95 (1H, m), 5.22 (1H, m), 6.95-7.14 (7H, m), 7.41 (0.4H, s), 7.50 (0.6H, s)

HPLC/MS: MH⁺=637.2

Step 2:

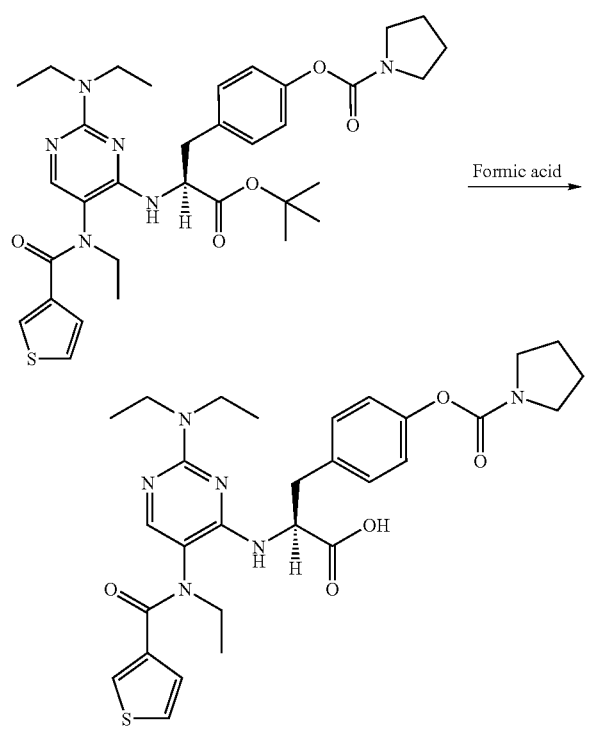

¹H NMR (300 MHz, CDCl₃), δ 0.70-1.4 (9H, m), 1.81-2.08 (4H, m), 2.62-4.10 (12H, m), 4.95 (1H, br s), 6.90-8.07 (8H, m)

HPLC/MS: MH⁺=581.2

Example 5

Preparation of N-[2-diethylamino-5-{N-ethyl-N-(furan-2-ylcarbonyl)amino}pyrimidin-4-yl]-L-4'-{(pyrrolidin-1-yl)carbonyloxy}phenylalanine Step 1:

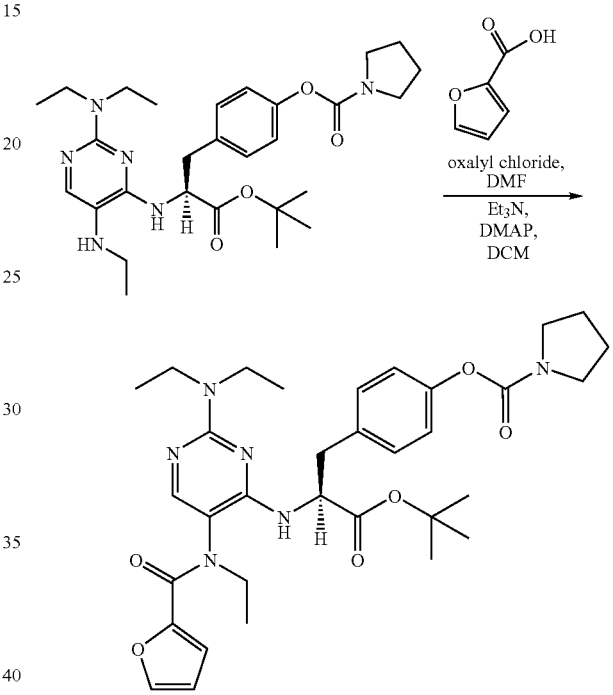

¹H NMR (300 MHz, CDCl₃) δ 1.15-1.28 (9H, m), 1.37 (3.6H, s), 1.42 (5.4H, s), 1.93-2.05 (4H, m), 2.85-3.15 (2H, m), 3.19-3.35 (1H, m), 3.45-3.75 (8H, m), 3.90-4.15 (1H, m), 4.76-4.85 (0.4H, m), 4.90-5.00 (0.6H, m), 5.15-5.22 (1H, m), 6.20-6.40 (2H, m), 6.91-7.18 (4H, m), 7.39 (1H, s), 7.58 (0.4H, s), 7.65 (0.6H, s)

HPLC/MS: MH⁺=621.3

Step 2:

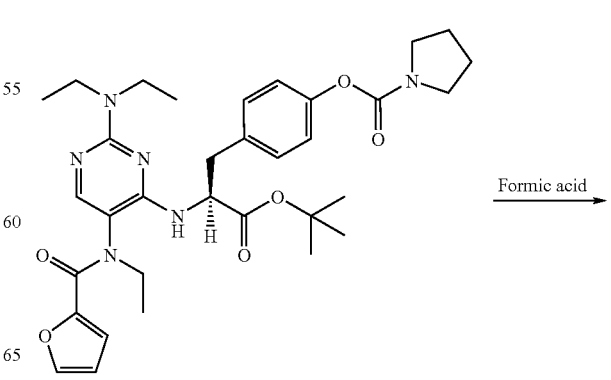

-continued

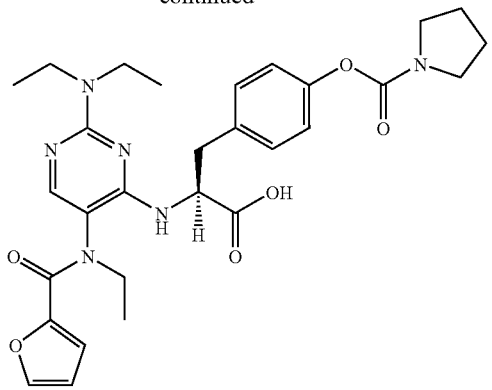

¹H NMR (300 MHz, CD₃OD) δ 0.84-1.25 (9H, m), 1.85-1.92 (4H, m), 2.70-2.81 (0.5H, m), 2.92-3.30 (2.5H, m, overlap with CD₃OD), 3.30-3.38 (2H, m), 3.45-3.59 (6H, m), 4.04-4.12 (1 H, m), 4.80-4.89 (1H, overlap with CD₃OD), 6.18 (1H, m), 6.58 (0.5H, br s), 6.78 (0.5H, br s), 6.83 (1H, d, J=8.1 Hz), 6.92 (1H, m), 7.06(1H, d, J=8.1 Hz), 7.19 (1H, d, J=8.1 Hz), 7.38 (0.5H, br s), 7.44 (0.5H, s), 7.47 (0.5H, br s), 7.48 (0.5H, s)

HPLC/MS: MH⁺=565.2

Example 6

Preparation of N-[2-diethylamino-5-{N-ethyl-N-(t-butylcarbonyl)amino}pyrimidin-4-yl]-L-4'-{(pyrrolidin-1-yl)carbonyloxy}phenylalanine Step 1:

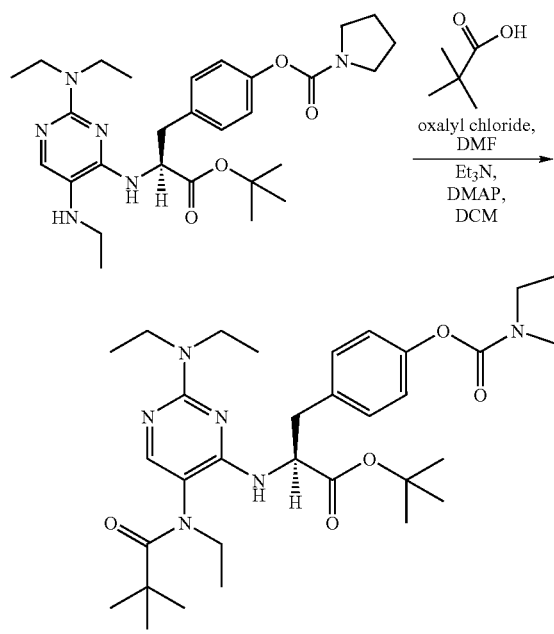

¹H NMR (300 MHz, CDCl₃) δ 1.04-1.11 (18H, m), 1.40 (4.5H, s), 1.42 (4.5H, s), 1.96 (4H, m), 2.46-2.59 (0.5H, m), 2.72-2.85 (0.5H, m), 3.00-3.32 (2H, m), 3.45-3.62 (8H, m), 3.82-4.15 (1H, m), 4.82-4.93 (1H, m), 5.05 (0.5H, d, J=7.2 Hz), 5.15 (0.5H, d, J=7.2 Hz), 7.08-7.18 (4H, m), 7.67 (1H, s)

HPLC/MS: MH⁺=611.3

Step 2:

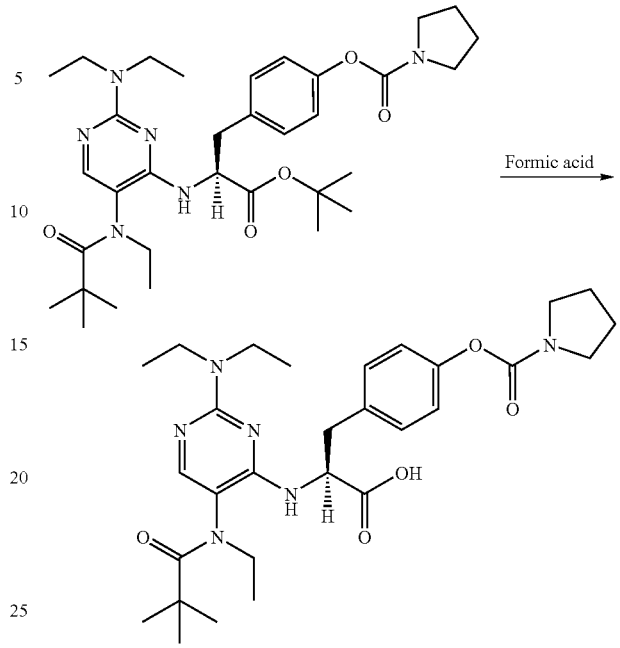

¹H NMR (300 MHz, CD₃OD) δ 0.86-1.20 (18H, m), 1.87 (4H, m), 2.32-2.45 (0.5H, m), 2.56-2.68 (0.6H, m), 3.05-3.20 (2H, m), 3.29-3.38 (2H, m), 3.43-3.52 (6H, m), 3.8-3.99 (1H, m), 4.75-4.82 (1H, overlap with CD₃OD), 6.90 (2H, d, J=9.0 Hz), 7.15 (2H, d, J=9.0 Hz), 7.43 (1H, s)

HPLC/MS: MH⁺=555.2

Example 7

Preparation of N-[2-diethylamino-5-{N-ethyl-N-(iso-propylcarbonyl)amino}pyrimidin-4-yl]-L-4'-{(pyrrolidin-1-yl)carbonyloxy}phenylalanine Step 1:

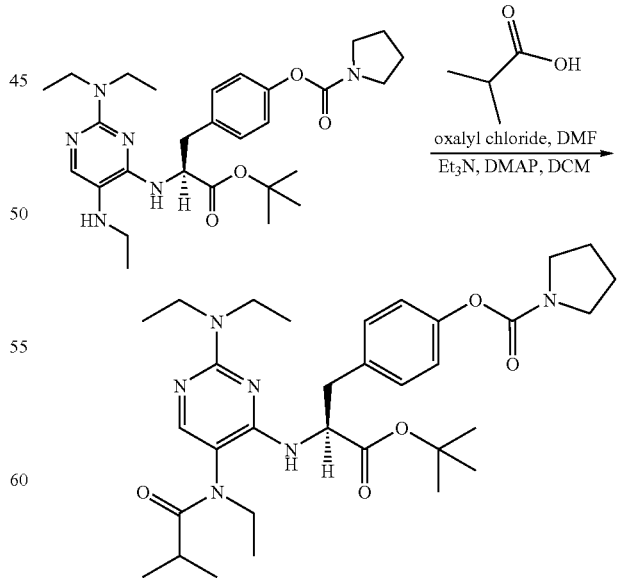

¹H NMR (300 MHz, CDCl₃) δ 0.90-1.21 (15H, m), 1.38 (9H, s), 1.92 (4H, m), 2.28-2.50 (1H, m), 2.80-3.16 (3H, m), 3.41-3.70 (8H, m), 3.80-3.95 (1H, m), 4.71-4.85 (1H, m), 5.05-5.11 (1H, m), 7.00-7.08 (2H, m), 7.08-7.16 (2H, m), 7.65 (1H, d, J=5.0 Hz)

HPLC/MS: MH+=597.3

Step 2:

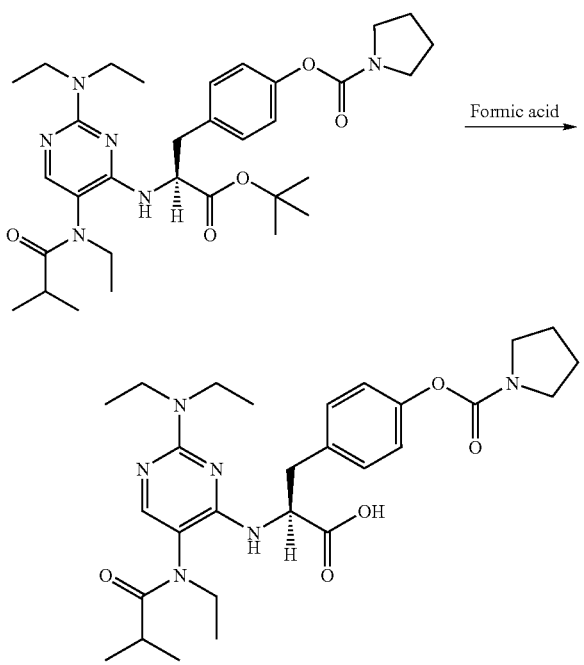

$^1$H NMR (300 MHz, CD$_3$OD) δ 0.80-0.98 (9H, m), 1.15-1.19 (6H, m), 1.88 (4H, m), 2.20-2.42 (1H, m), 2.65-2.83 (1H, m), 3.08-3.25 (2H, m), 3.26-3.59 (8H, m), 3.88-3.97 (1H, m), 4.70-5.05 (1H, overlap with CD$_3$OD), 6.92 (2H, d, J=7.8 Hz), 7.17 (2H, m), 7.63 (1H, d, J=5.0 Hz)

HPLC/MS: MH+=541.3

Example 8

General Method for the Preparation of Pyrimidinyl Ureas

Step 1:

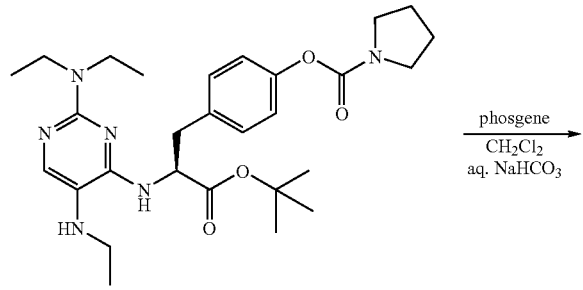

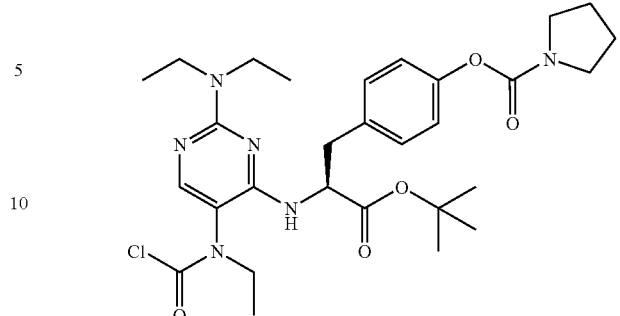

N-[2-diethylamino-5-{N-ethylamino}pyrimidin-4-yl]-L-4'-{(pyrrolidin-1-yl)carbonyloxy}phenylalanine tert-butyl ester (0.436 g, 0.83 mmol) was dissolved in CH$_2$Cl$_2$ (0.35 mL) and sat. NaHCO$_3$ (0.7 mL). The solution was cooled to zero degrees and vigorously stirred for 10 minutes. After 10 minutes the stirring was stopped and the immiscible layers were allowed to separate. Phosgene (0.52 mL, 4.97 mmol) was added to the bottom layer via syringe. The reaction mixture was stirred under N$_2$ for three hours. Upon completion, the organic layer was separated and it was concentrated in vacuo at rt. It was redissolved in EtOAc and washed with de-ionized water and back extracted two times. The organic layer was dried over Na$_2$SO$_4$ and concentrated in vacuo. The crude oil was taken forward to the next step without purification.

HPLC/MS: MH+=589.0

Step 2:

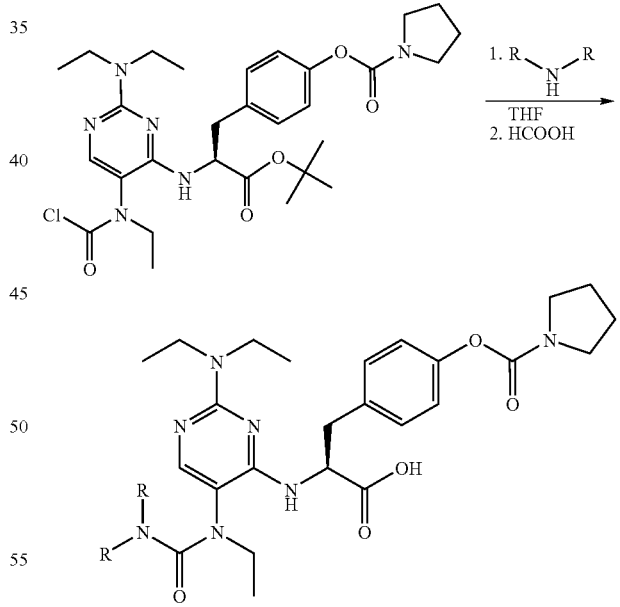

Crude carbamyl chloride (1 eq.) and amine (5 eq.) were dissolved in THF (0.2M) and stirred over night under N$_2$. The reaction mixture was concentrated in vacuo and redissolved in ethyl acetate. The organic layer was washed with water, dried over Na$_2$SO$_4$ and concentrated in vacuo. The products were purified by HPLC. The products were treated with HCOOH as solvent at 40° C. overnight. The solvent was removed under reduced pressure and the products were obtained Examples 9-11 were prepared according to example 8. .

Example 9

Preparation of N-[2-diethylamino-5-{N-ethyl-N-(piperidin-1-ylcarbonyl)amino} pyrimidin-4-yl]-L-4'-{(pyrrolidin-1-yl)carbonyloxy}phenylalanine

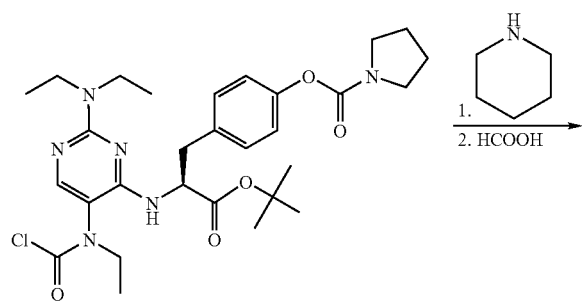

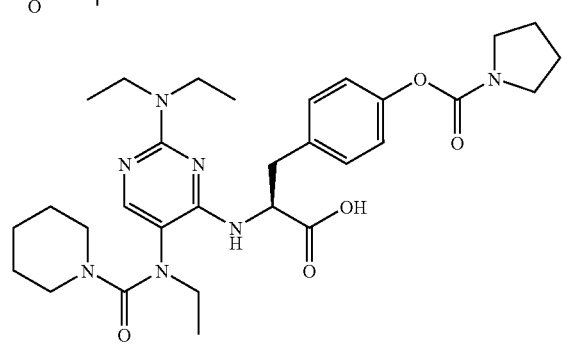

$^1$H NMR (300 MHz, CDCl$_3$) δ 1.01 (3H, t, J=7 Hz), 1.22 (6H, t, J=7 Hz), 1.36 (4H, m), 1.49 (2H, m), 1.95 (4H, m), 3.10-3.66 (16H, m), 4.86-4.92 (1H, m), 6.75 (1H, d, J=7.2 Hz), 7.25 (2H, d, J=8.4 Hz), 7.14(2H, d, J=8.4 Hz), 7.64 (1H, s).

HPLC/MS: MH$^+$=582.3

Example 10

Preparation of N-[2-diethylamino-5-{N-ethyl-N-(N-ethyl-N-isopropylaminocarbonyl)amino}pyrimidin-4-yl]-L-4'-{(pyrrolidin-1-yl)carbonyloxy}phenylalanine

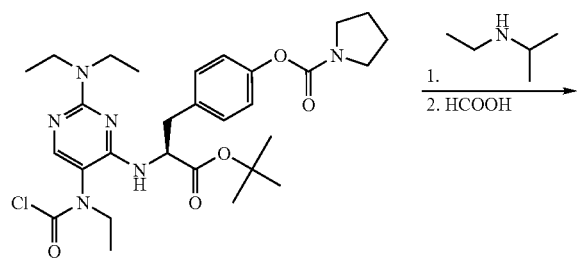

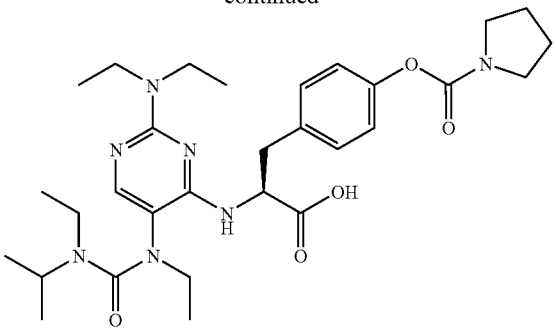

$^1$H NMR (300 MHz, CDCl$_3$) δ 1.01 (9H, br s), 1.21 (9H, m), 1.90-1.99 (4H, m), 2.98 (2H, m), 3.15 (3H, m), 3.33 (1H, m), 3.45 (2H, m), 3.52-3.60 (6H, m), 3.76 (1H, m), 4.91-4.97 (1H, br s), 6.64 (1H, br s), 7.04 (2H, d, J=8 Hz), 7.14 (2H, d, J=8 Hz), 7.66 (1H, s).

HPLC/MS: MH$^+$=584.4

Example 11

Preparation of N-[2-diethylamino-5-{N-ethyl-N-(3-thiapyrrolidin-1-ylcarbonyl)amino}pyrimidin-4-yl]-L-4'-{(pyrrolidin-1-yl)carbonyloxy} phenylalanine

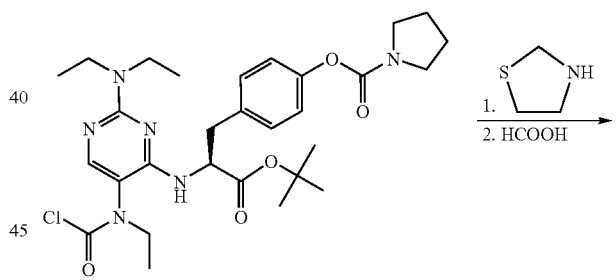

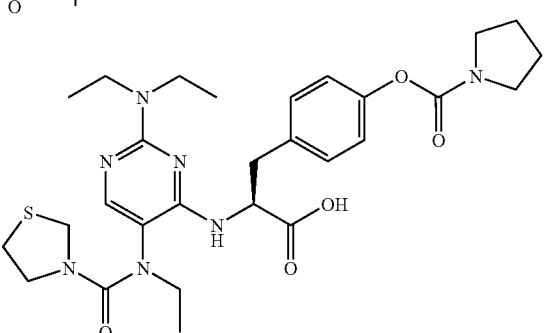

$^1$H NMR (300 MHz, CDCl$_3$) δ 1.03 (3H, t, J=6.6 Hz), 1.21 (6H, t, J=6.6 Hz), 1.90-1.99 (4H, m), 2.84 (2H, t, J=6 Hz), 3.09-3.63 (14H, m), 4.06-4.14 (2H, q, J=7.8 Hz), 4.91-4.97 (1H, m), 6.64 (1H, d, J=7 Hz), 7.04 (2H, d, J=8.4 Hz), 7.13 (2H, d, J=8.4 Hz), 7.75 (1H, s).

HPLC/MS: MH$^+$=586.2

Example A

α4β1 Integrin Adhesion Assay: Jurkat Cell Adhesion to Human Plasma Fibronectin

Procedure 96 well plates (Costar 3590 EIA plates) were coated with human fibronectin (Gibco/BRL, cat #33016-023) at a concentration of 10 μg/mL overnight at 4° C. The plates were then blocked with a solution of bovine serum albumin (BSA; 0.3%) in saline. Jurkat™ cells (maintained in log phase growth) were labeled with Calcein AM according to the manufacturer's instructions, and suspended at a concentration of $2 \times 10^6$ cells/mL in Hepes/Saline/BSA. The cells were then exposed to test and control compounds for 30 minutes at room temperature before transfer to individual wells of the fibronectin coated plate. Adhesion was allowed to occur for 35 minutes at 37° C. The wells were then washed by gentle aspiration and pipetting with fresh saline. Fluorescence associated with the remaining adherent cells was quantified using a fluorescence plate reader at EX 485/EM 530.

Cell cultures were prepared by first splitting the stationary phase Jurkat™ cells at 1:10 on day one, and 1:2 on day two to perform assay on day 3. The cells split 1:10 on day one were split 1:4 on day 3 for a day 4 assay.

The assay plates were prepared by first making a working solution of Gibco/BRL Human Fibronectin (cat #33016-023) in PBS++, at 10 μg/mL.

A Costar 3590 EIA plate was then coated with 50 μL/well for 2 hours at room temperature (though it can also be left overnight at 4° C.). Finally the plate was aspirated and blocked with Hepes/Saline Buffer, 100 μL/well, for 1 hour at rt followed by washing three times with 150 μL of PBS++.

Compound dilutions were accomplished by preparing 1:3 serial dilutions of compounds as follows. For each plate (4 compounds/plate) 600 μL were added to 4 Bio-Rad Titertubes in a Titertube rack. Enough compound was added to each appropriate tube to give a 2x concentration using methods well known in the art. Using Falcon Flexiplates, 100 μL of Hepes/Saline buffer or human serum were added to rows B through G. A multi-channel pipetter set to 180 μL was used to with four tips spaced evenly on the pipetter. Each set of four tubes was mixed 5 times and 180 μL of 2x compound was transferred to the first column of each compound dilution in Row B, leaving Row A empty. 180 μL were added to the other wells in Row A. Serial dilutions were performed down the plate by transferring 50 μL to the next dilution and mixing 5 times, changing tips each time after mixing. Dilutions were stopped at Row F. Row G had no compound present.

A 20 μg/ml solution in Hepes/Saline buffer or human serum, of 21/6 antibody was the positive control and was set aside in a reagent trough to add to cell suspension plate.

The cell staining was accomplished by first harvesting the log-phase Jurkat™ cells by centrifugation in 50 mL tubes (1100 rpm for 5 minutes). The cells were resuspended in 50 mL PBS++, spun, and resuspended in 20 mL PBS++. The cells were stained by adding 20 μL of Calcein AM for 30 minutes at RT. The volume was brought to 50 mL with Hepes/Saline buffer and the cells were counted, spun, and resuspended to $2 \times 10^6$ cells/mL in Hepes/Saline buffer or human serum.

The compounds were incubated using the following procedure. In a new flexiplate, 65 μL of stained cells were added to Rows B through H. Then 65 μL of 2x compounds were added to the appropriate rows following the plate setup and mixed 3x. 65 μL of 2x-21/6 antibody were added to Row H and mixed 3x. Finally the plate was incubated at room temperature for 30 minutes.

Fibronectin adhesion was measured using a fluorescent plate reader at EX 485/EM 530 after the following work up procedure. After incubation, the cells were mixed 3x and 100 μL were transferred to the Fibronectin coated plates and incubated at 37° C. for about 35 minutes. Each plate was washed, row by row, by gently pipetting 100 μL of RT PBS++ down the sides of the wells and turning the plate 90 degrees to aspirate. This procedure was repeated for a total of 3 washes. Each well was filled with 100 μL after washing by pipetting down the side of the well.

An $IC_{50}$ value was calculated for each compound, both in the presence of the human serum and in the absence of human serum. $IC_{50}$ is concentration at which the growth or activity is inhibited by 50%. The compounds disclosed herein were all found to have an $IC_{50}$ of less than 10 μM when tested according to the fibronectin assay.

Example B

Cell Adhesion to Human Plasma Fibronectin. In Vitro Saturation Assay for Determining Binding of Candidate Compounds to α4β1

The following describes an in vitro assay to determine the plasma levels needed for a compound to be active in the Experimental Autoimmune Encephalomyelitis ("EAE") model, described in the next example, or in other in vivo models.

Log-growth Jurkat™ cells are washed and resuspended in normal animal plasma containing 20 μg/mL of the 15/7 antibody (Yednock, et al., J. Biol. Chem., (1995) 270(48):28740).

The Jurkat™ cells are diluted two-fold into either normal plasma samples containing known candidate compound amounts in various concentrations ranging from 66 μM to 0.01 μM, using a standard 12 point serial dilution for a standard curve, or into plasma samples obtained from the peripheral blood of candidate compound-treated animals.

Cells are then incubated for 30 minutes at room temperature, washed twice with phosphate-buffered saline ("PBS") containing 2% fetal bovine serum and 1 mM each of calcium chloride and magnesium chloride (assay medium) to remove unbound 15/7 antibody.

The cells are then exposed to phycoerythrin-conjugated goat F(ab')2 anti-mouse IgG Fc (Immunotech, Westbrook, Me.), which has been adsorbed for any non-specific cross-reactivity by co-incubation with 5% serum from the animal species being studied, at 1:200 and incubated in the dark at 4° C. for 30 minutes.

Cells are washed twice with assay medium and resuspended in the same. They are then analyzed with a standard fluorescence activated cell sorter ("FACS") analysis as described in Yednock et al., J. Biol. Chem., 1995, 270:28740.

The data is then graphed as fluorescence versus dose, e.g., in a normal dose-response fashion. The dose levels that result in the upper plateau of the curve represent the levels needed to obtain efficacy in an in vivo model.

This assay may also be used to determine the plasma levels needed to saturate the binding sites of other integrins, such as the $α_9β_1$ integrin, which is the integrin most closely related $α_4β_1$ (Palmer et al., 1993, J. Cell Bio., 123:1289). Such binding is predictive of in vivo utility for inflammatory conditions mediated by ago, integrin, including by way of example, airway hyper-responsiveness and occlusion that occurs with chronic asthma, smooth muscle cell proliferation in atherosclerosis, vascular occlusion following angioplasty, fibrosis and glomerular scarring as a result of renal disease, aortic stenosis, hypertrophy of synovial membranes in rheumatoid arthritis, and inflammation and scarring that occur with the progression of ulcerative colitis and Crohn's disease.

Accordingly, the above-described assay may be performed with a human colon carcinoma cell line, SW 480 (ATTC #CCL228) transfected with cDNA encoding $\alpha_9$ integrin (Yokosaki et al., 1994, J. Biol. Chem., 269:26691), in place of the Jurkat cells, to measure the binding of the $\alpha_9\beta_1$ integrin. As a control, SW 480 cells which express other $\alpha$ and $\beta_1$ subunits may be used.

Accordingly, another aspect of this invention is directed to a method for treating a disease in a mammalian patient, which disease is mediated by ago $\alpha_9\beta_1$, and which method comprises administering to said patient a therapeutically effective amount of a compound of this invention. Such compounds are preferably administered in a pharmaceutical composition described herein above. Effective daily dosing will depend upon the age, weight, condition of the patient which factors can be readily ascertained by the attending clinician. However, in a preferred embodiment, the compounds are administered from about 20 to 500 µg/kg per day.

Example C

Cassette Dosing and Serum Analysis for Determination of Bioavailability

The oral bioavailability is screened by dosing rats with a cassette, i.e. mixture of 6 compounds per dosing solution. The cassette includes 5 test articles and a standard compound, for a total dose of 10 mg/kg. Each compound/test article is converted to the sodium salt with equimolar 1 N NaOH and dissolved in water at 2 mg/mL. The cassette is prepared by mixing equal volumes of each of the six solutions. The cassette dosing solution is mixed well and then the pH was adjusted to 7.5-9. The dosing solution is prepared the day before the study and is stirred overnight at room temperature.

Male Sprague Dawley (SD) rats from Charles River Laboratories, 6-8 weeks old, are used in this screen. Rats are quarantined for at least one day and had continuous access to food and water. On the night before the administration of the cassette, the rats are fasted for approximately 16 h.

Four SD rats are assigned in each cassette. A single dose of the dosing solution is administered orally to each rat. The dosing volume (5 mL/kg) and time are recorded and rats are fed 2 h after dosing.

Blood samples are collected via cardiac puncture at the following time points: 4 h, 8 h and 12 h. Immediately prior to blood collection, rats are anesthetized with $CO_2$ gas within 10-20 seconds. After the 12-hour samples are collected, the rats are euthanized via $CO_2$ asphyxiation followed by cervical dislocation.

Blood samples are kept in heparinized microtainer tubes under sub-ambient temperature (4° C.) before they are processed. Blood samples are centrifuged (10000 rpm for 5 minutes) and plasma samples are removed and stored in a −20° C. freezer until analyzed for drug levels. Drug levels in the plasma are analyzed using the following protocol for direct plasma precipitation.

The in vivo plasma samples are prepared in a 1.5 mL 96-well plate, by adding, in order, 100 µL of the test plasma, 150 µl of methanol, followed by vortexing for 10-20 seconds. 150 µL of 0.05 ng/µL of an Internal Standard in acetonitrile were added and vortexed for 30 seconds.

The standard curve samples were prepared in a 1.5 mL 96-well plate, by adding, in order, 100 µL of control mouse plasma, followed by 150 µL of methanol and vortexing for 10-20 seconds. 150 µL of 0.05 ng/µL of an Internal Standard in acetonitrile were added and vortexed for 30 seconds. The samples were spiked with 0-200 ng (10 concentrations) of the compound of interest in 50% methanol to obtain a standard curve range of 0.5 ng/mL to 2,000 ng/mL. Again, the sample is vortexed for 30 seconds.

The samples are then spun for 20-30 minutes at 3000 rpm in an Eppendorf microfuge before 80-90% of supernatant is transferred into a clean 96-well plate. The organic solvent is then evaporated until the samples are dry (under $N_2$ at 40° C./30-60 min. (ZymarkTurbovap)).

The residue is then dissolved in 200-600 L mobile phase (50% $CH_3OH$/0.1% TFA). LC/MS/MS is then run using a PE-Sciex API-3000 triple quadurpole mass spectrometer (SN0749707), Perkin-Elmer, Series200auto-sampler, and Shimadzu 10A pump. Acquisition is done with PE-Sciex Analyst (v 1.1) and data analysis and quantification are accomplished using PE-Sciex Analyst (v 1.1). A 5-50 µl sample volume was injected onto a reverse phase ThermoHypersil DASH-18 column (Keystone 2.0×20 mm, 5 µm, PN: 8823025-701) using a mobile phase of 25% $CH_3OH$, 0.1% TFA-100% $CH_3OH$, 0.1% TFA. The run time is about 8 minutes at a flow rate of about 300 µL/minutes.

The Area Under the Curve (AUC) is calculated using the linear trapezoidal rule from t=0 to the last sampling time tx (see Handbook of Basic Pharmacokinetics, Wolfgang A. Ritschel and Gregory L. Kearns, 5th ed, 1999).

$$AUC^{0 \to tx} = \chi((C_n+C_{n+1})/2))\chi(t_{n+1}-t_n)[(\mu g/mL)h]$$

In the case of the cassette dosing paradigm, samples at 4, 8 and 12 h post extravascular dosing, the AUC is calculated from t=0 to t=12 h.

Example D

Asthma Models

Inflammatory conditions mediated by $\alpha_4\beta_1$ integrin include, for example, eosinophil influx, airway hyper-responsiveness and occlusion that occurs with chronic asthma. The following describes animal models of asthma that are used to study the in vivo effects of the compounds of this invention for use in treating asthma.

Rat Asthma Model

Following the procedures described by Chapman, et al., Am J. Resp. Crit. Care Med., 153-4, A219 (1996) and Chapman, et al., Am. J. Resp. Crit. Care Med. 155:4, A881 (1997), both of which are incorporated by reference in their entirety.

Ovalbumin (OA; 10 µg/mL) is mixed with aluminum hydroxide (10 mg/mL) and injected (i.p.) in Brown Norway rats on day 0. Injections of OA, together with adjuvant, are repeated on days 7 and 14. On day 21, sensitized animals are restrained in plastic tubes and exposed (60 minutes) to an aerosol of OA (10 mg/kg) in a nose-only exposure system. Animals are sacrificed 72 hours later with pentobarbital (250 mg/kg, i.p.). The lungs are lavaged via a tracheal cannula using 3 aliquots (4 mL) of Hank's solution (HBSS×10, 100 ml; EDTA 100 mM, 100 mL; HEPES 1 M, 25 mL; made up to 1 L with $H_2O$); recovered cells are pooled and the total volume of recovered fluid adjusted to 12 mL by addition of Hank's solution. Total cells are counted (Sysmex microcell counter F-500, TOA Medical Electronics Otd., Japan) and smears are made by diluting recovered fluid (to approximately 106 cells/mL) and pipetting an aliquot (100 μl) into a centrifuge (Cytospin, Shandon, U.K.). Smears are air dried, fixed using a solution of fast green in methanol (2 mg/mL) for 5 seconds and stained with eosin G (5 seconds) and thiazine (5 seconds) (Diff-Quick, Browne Ltd. U.K.) in order to differentiate eosinophils, neutrophils, macrophages and lymphocytes. A total of 500 cells per smear are counted by light microscopy under oil immersion (×100). Compounds of this invention can be formulated into a 0.5% carboxymethylcellulose and 2% Tween 80 suspension and administered orally to rats which had been sensitized to the allergen, ovalbumin. Compounds which inhibited allergen-induced leucocyte accumulation in the airways of actively sensitized Brown Norway rats are considered to be active in this model.

Mouse Asthma Model

Compounds are also evaluated in a mouse model of acute pulmonary inflammation following the procedures described by, Kung, et al., Am J. Respir. Cell Mol. Biol., 13:360-365, (1995) and Schneider, et al., (1999). Am J. Respir. Cell Mol. Biol. 20:448-457, (1999), which are each incorporated by reference in their entirety. Female Black/6 mice (8-12 weeks of age) are sensitized on day 1 by an intraperitoneal injection (i.p.) of 0.2 mL ova/alum mixture containing 20 μg of ova (Grade 4, Sigma) and 2 mg inject Alum (Pierce). A booster injection is administered on day 14. Mice are challenged on days 28 and 29 with aerosolized 1% ova (in 0.9% saline) for 20 minutes. Mice are euthanized and bronchaveolar lavage samples (3 mL) are collected on day 30, 48 hours post first challenge. Eosinophils are quantified by a FACs/FITC staining method. Compounds of this invention are formulated into a 0.5% carboxymethylcellulose and 2% Tween 80 suspension and administered orally to mice which had been sensitized to the allergen, ovalbumin. Compounds which inhibited allergen-induced leucocyte accumulation in the airways of actively sensitized C57BL/6 mice are considered to be active in this model.

Sheep Asthma Model

This model employs the procedures described by Abraham, et al., J. Clin, Invest, 93:776-787 (1994) and Abraham, et al., Am J. Respir. Crit. Care Med., 156:696-703 (1997), both of which are incorporated by reference in their entirety. Compounds of this invention are evaluated by intravenous (saline aqueous solution), oral (2% Tween 80, 0.5% carboxymethylcellulose), and aerosol administration to sheep which are hypersensitive to *Ascaris suum* antigen. Compounds which decrease the early antigen-induced bronchial response and/or block the late-phase airway response, e.g. have a protective effect against antigen-induced late responses and airway hyper-responsiveness ("AHR"), are considered to be active in this model.

Allergic sheep which are shown to develop both early and late bronchial responses to inhaled *Ascaris suum* antigen are used to study the airway effects of the candidate compounds. Following topical anesthesia of the nasal passages with 2% lidocaine, a balloon catheter is advanced through one nostril into the lower esophagus. The animals are then incubated with a cuffed endotracheal tube through the other nostril with a flexible fiberoptic bronchoscope as a guide.

Pleural pressure is estimated according to Abraham (1994). Aerosols (see formulation below) are generated using a disposable medical nebulizer that provided an aerosol with a mass median aerodynamic diameter of 3.2 μm as determined with an Andersen cascade impactor. The nebulizer is connected to a dosimeter system consisting of a solenoid valve and a source of compressed air (20 psi). The output of the nebulizer is directed into a plastic T-piece, one end of which is connected to the inspiratory port of a piston respirator. The solenoid valve is activated for 1 second at the beginning of the inspiratory cycle of the respirator. Aerosols are delivered at VT of 500 mL and a rate of 20 breaths/minute. A 0.5% sodium bicarbonate solution only is used as a control.

To assess bronchial responsiveness, cumulative concentration-response curves to carbachol is generated according to Abraham (1994). Bronchial biopsies are taken prior to and following the initiation of treatment and 24 hours after antigen challenge. Bronchial biopsies are preformed according to Abraham (1994).

An in vitro adhesion study of alveolar macrophages can also be performed according to Abraham (1994), and a percentage of adherent cells can be calculated.

Aerosol Formulation

A solution of the candidate compound in 0.5% sodium bicarbonate/saline (w/v) at a concentration of 30.0 mg/mL is prepared using the following procedure:

A. Preparation of 0.5% Sodium Bicarbonate/Saline Stock Solution: 100.0 mL

| Ingredient | Gram/100.0 mL | Final Concentration |
|---|---|---|
| Sodium Bicarbonate | 0.5 g | 0.5% |
| Saline | q.s. ad 100.0 mL | q.s. ad 100% |

Procedure:

1. Add 0.5 g sodium bicarbonate into a 100 mL volumetric flask.
2. Add approximately 90.0 mL saline and sonicate until dissolved.
3. Q.S. to 100.0 mL with saline and mix thoroughly.

B. Preparation of 30.0 mg/mL Candidate Compound: 10.0 mL

| Ingredient | Gram/10.0 mL | Final Concentration |
|---|---|---|
| Candidate Compound | 0.300 g | 30.0 mg/mL |
| 0.5% Sodium Bicarbonate/Saline Stock Solution | q.s. ad 10.0 mL | q.s ad 100% |

Procedure:

1. Add 0.300 g of the candidate compound into a 10.0 mL volumetric flask.
2. Add approximately 9.7 mL of 0.5% sodium bicarbonate/saline stock solution.
3. Sonicate until the candidate compound is completely dissolved.
4. Q.S. to 10.0 mL with 0.5% sodium bicarbonate/saline stock solution and mix thoroughly.

Example E

10-Day Toxicity Study on C57B6 Mice

A 10-day study is conducted to evaluate the toxicity of compounds of the present invention to female C57B6 mice.

The compound is administered by gavage at five dose levels, 0 (vehicle control), 10, 30, 100, 300 and 1000 mg/kg (mpk), with five mice in each dose level. The dose volume for all levels was 10 mL/kg. Dose solutions or suspensions are prepared in 2% Tween 80 in 0.5% carboxymethyl cellulose (CMC) and new dose solutions or suspensions are prepared every two-three days. In-life observations include body weights (study day 1, 2, 3, 5, 7, 8 and 11), daily cageside clinical observations (1-2/day) and periodic (study day—1, 2 and 9) functional observation battery.

At termination, blood samples are collected by cardiac puncture for clinical pathology (hematology and clinical chemistry) and drug levels. The EDTA blood samples are analyzed for total white blood cell count, red blood cell count, hemoglobin, hematocrit, erythrocyte indices (MCV, MCH, MCHC), platelets and a WBC five part differential (neutrophil, lymphocytes, monocytes, eosinophils and basophils). Heparinized plasma samples are analyzed for alanine transaminase, aspartate transaminase, alkaline phosphatase, total bilirubin, albumin, protein, calcium, glucose, urea nitrogen, creatinine, cholesterol and triglycerides.

After blood collection, the carcass is necropsied and organs (liver, spleen, kidneys, heart and thymus) are weighed. Tissue samples; brain, salivary glands, thymus, heart, lung, liver, kidney, adrenal spleen, stomach, duodenum, ileum, colon and uterus/ovary, are collected and formalin fixed. Tissues from the vehicle control and 300 and 1000 mpk group animals are processed to H & E stained glass slides and evaluated for histopathological lesions.

Body weight changes, absolute and relative organ weights and clinical pathology results are analyzed for statistical significant differences compared to the vehicle controls by Dunnet's multiple comparison test using Prism software. The functional observation battery results are analyzed for differences using the Dunnet's, Fisher's exact tests and dose trend effects by the Cochran-Mantel-Haenszel correlation test using SAS software.

Using a conventional oral formulation, compounds of this invention would be active in this model.

Example F

Adjuvant-Induced Arthritis in Rats

Adjuvant induced arthritis ("AIA") is an animal model useful in the study of rheumatoid arthritis (RA), which is induced by injecting *M. tuberculosis* in the base of the tail of Lewis rats. Between 10 and 15 days following injection, animals develop a severe, progressive arthritis.

Generally, compounds are tested for their ability to alter hind paw swelling and bone damage resulting from adjuvant induced edema in rats. To quantitate the inhibition of hind paw swelling resulting from AIA, two phases of inflammation have been defined: (1) the primary and secondary injected hind paw, and (2) the secondary uninjected hind paw, which generally begins developing about eleven days from the induction of inflammation in the injected paw. Reduction of the latter type of inflammation is an indication of immunosuppressive activity. Cf. Chang, Arth. Rheum., 20, 1135 1141 (1977).

Using an animal model of RA, such as AIA, enables one to study the cellular events involved in the early stages of the disease. CD44 expression on macrophages and lymphocytes is up regulated during the early development of adjuvant arthritis, whereas LFA 1 expression is up regulated later in the development of the disease. Understanding the interactions between adhesion molecules and endothelium at the earliest stages of adjuvant arthritis could lead to significant advances in the methods used in the treatment of RA.

The following compounds were all found to have an $IC_{50}$ at less than about 10 μM when tested according to the fibronectin Assay Example A:

N-[2-diethylamino-5-{N-ethyl-N-(trifluoroacetyl) amino}pyrimidin-4-yl]-L-4'-{(pyrrolidin-1-yl) carbonyloxy}phenylalanine;

N-[2-diethylamino-5-{N-ethyl-N-(iso-propylcarbonyl) amino}pyrimidin-4-yl]-L-4'-{(pyrrolidin-1-yl) carbonyloxy}phenylalanine;

N-[2-diethylamino-5-{N-ethyl-N-(t-butylcarbonyl) amino}pyrimidin-4-yl]-L-4'-{(pyrrolidin-1-yl) carbonyloxy}phenylalanine;

N-[2-diethylamino-5-{N-ethyl-N-(furan-2-ylcarbonyl) amino} pyrimidin-4-yl]-L-4'-{(pyrrolidin-1-yl) carbonyloxy}phenylalanine;

N-[2-diethylamino-5-{N-ethyl-N-(piperidin-1-ylcarbonyl) amino}pyrimidin-4-yl]-L-4'-{(pyrrolidin-1-yl)carbonyloxy} phenylalanine;

N-[2-diethylamino-5-{N-ethyl-N-(N-ethyl-N-isopropylaminocarbonyl)amino}pyrimidin-4-yl]-L-4'-{(pyrrolidin-1-yl)carbonyloxy} phenylalanine;

N-[2-diethylamino-5-{N-ethyl-N-(thien-3-ylcarbonyl) amino}pyrimidin-4-yl]-L-4'-{(pyrrolidin-1-yl) carbonyloxy}phenylalanine;

N-[2-diethylamino-5-{N-ethyl-N-(thien-2-ylcarbonyl) amino} pyrimidin-4-yl]-L-4'-{(pyrrolidin-1-yl) carbonyloxy}phenylalanine;

N-[2-diethylamino-5-{N-ethyl-N-(furan-3-ylcarbonyl) amino} pyrimidin-4-yl]-L-4'-{(pyrrolidin-1-yl) carbonyloxy}phenylalanine;

N-[2-diethylamino-5-{N-ethyl-N-(3-thiapyrrolidin-1-ylcarbonyl)amino} pyrimidin-4-yl]-L-4'-{(pyrrolidin-1-yl) carbonyloxy}phenylalanine;

N-[2-diethylamino-5-{N-ethyl-N-(thien-2-ylcarbonyl) amino}pyrimidin-4-yl]-L-4'-{(pyrrolidin-1-yl)carbonyloxy}-phenylalanine t-butyl ester;

N-[2-diethylamino-5-{N-ethyl-N-trifluoromethylcarbonyl) amino}pyrimidin-4-yl]-L-4'-{(pyrrolidin-1-yl)carbonyloxy}-phenylalanine t-butyl ester;

N-[2-diethylamino-5-{N-ethyl-N-t-butylcarbonyl)amino} pyrimidin-4-yl]-L-4'-{(pyrrolidin-1-yl)carbonyloxy}-phenylalanine t-butyl ester; and N-[2-diethylamino-5-{N-ethyl-N-furan-3-ylcarbonyl) amino}pyrimidin-4-yl]-L-4'-{(pyrrolidin-1-yl)carbonyloxy}-phenylalanine t-butyl ester.

While preferred embodiments of the invention have been illustrated and described, it will be appreciated that various changes can be made therein without departing from the spirit and scope of the invention

What is claimed is:

1. A compound of formula I:

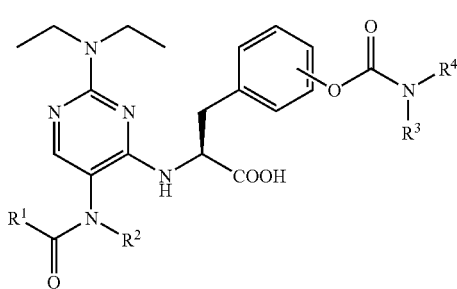

wherein:
R¹ is selected from the group consisting of $C_1$ to $C_4$ alkyl, $C_1$ to $C_4$ haloalkyl, heteroaryl, and —NR⁵R⁶ wherein R⁵ and R⁶ are independently selected from the group consisting of hydrogen and $C_1$ to $C_4$ alkyl, or R⁵ and R⁶ together with the nitrogen atom pendent thereto form a heterocyclic ring;
R² is selected from the group consisting of $C_1$ to $C_4$ alkyl, $C_2$ to $C_4$ alkenyl, and $C_2$ to $C_4$ alkynyl; and
R³ and R⁴ are independently $C_1$ to $C_3$ alkyl or R³ and R⁴ together with the nitrogen atom pendent thereto join to form a heterocyclic ring;
or a pharmaceutically acceptable salt;
or an ester of the carboxylic acid alpha to the amino group thereof.

2. A compound of claim 1, wherein the —OC(O)NR³R⁴ group is in the para position of the phenyl ring.

3. A compound of claim 2, wherein R³ and R⁴ together with the nitrogen atom pendent thereto form a heterocyclic ring.

4. A compound of claim 3, wherein the heterocyclic ring is pyrrolidinyl.

5. A compound of claim 4, wherein R² is $C_1$ to $C_4$ alkyl.

6. A compound of claim 5, wherein R² is ethyl.

7. A compound of formula II:

wherein:
R⁷ is $C_1$ to $C_4$ alkyl, $C_1$ to $C_4$ haloalkyl, or heteroaryl;
R⁸ is $C_1$ to $C_4$ alkyl;
R⁹ and R¹⁰ are independently $C_1$ to $C_3$ alkyl, or R⁹ and R¹⁰ together with the nitrogen atom pendent thereto form a heterocyclic ring;
or a pharmaceutically acceptable salt;
or an ester of the carboxylic acid alpha to the amino group thereof.

8. A compound of claim 7 wherein the —OC(O)NR⁹R¹⁰ group is in the para position of the phenyl ring.

9. A compound of claim 8, wherein R⁹ and R¹⁰ together with the nitrogen atom pendent thereto form a heterocyclic ring.

10. A compound of claim 9, wherein the heterocyclic ring is pyrrolidinyl.

11. A compound of claim 10, wherein R⁸ is $C_1$ to $C_4$ alkyl.

12. A compound of claim 11, wherein R⁸ is ethyl.

13. A compound of claim 12, wherein R⁷ is $C_1$ to $C_4$ alkyl.

14. A compound of claim 13, wherein R⁷ is selected from the group consisting of isopropyl and t-butyl.

15. A compound of claim 12, wherein R⁷ is $C_1$ to $C_4$ haloalkyl.

16. A compound of claim 15, wherein R⁷ is trifluoromethyl.

17. A compound of claim 12, wherein R⁷ is heteroaryl.

18. A compound of claim 17, wherein R⁷ is selected from the group consisting of furan-2-yl, furan-3-yl, thien-2-yl, and thien-3-yl.

19. A compound of formula III:

wherein:
R¹¹ and R¹² are independently $C_1$ to $C_4$ alkyl, or R¹¹ and R¹² together with the nitrogen atom pendent thereto form a heterocyclic ring;
R¹³ is $C_1$ to $C_4$ alkyl; and
R¹⁴ and R¹⁵ are independently $C_1$ to $C_3$ alkyl or R¹⁴ and R¹⁵ together with the nitrogen atom pendent thereto form a heterocyclic ring;
or a pharmaceutically acceptable salt;
or an ester of the carboxylic acid alpha to the amino group thereof.

20. A compound of claim 19 wherein the —OC(O)NR¹⁴R¹⁵ group is in the para position of the phenyl ring.

21. A compound of claim 20, wherein R¹⁴ and R¹⁵ together with the nitrogen atom pendent thereto form a heterocyclic ring.

22. A compound of claim 21, wherein the heterocyclic ring is pyrrolidinyl.

23. A compound of claim 22, wherein R¹³ is $C_1$ to $C_4$ alkyl.

24. A compound of claim 23, wherein R¹³ is ethyl.

25. A compound of claim 24, wherein R¹¹ and R¹² are independently $C_1$ to $C_4$ alkyl.

26. A compound of claim 25, wherein R¹¹ is ethyl and R¹² is isopropyl.

27. A compound of claim 24, wherein R¹¹ and R¹² together with the nitrogen atom pendent thereto form a heterocyclic ring.

28. A compound of claim 27, wherein said heterocyclic ring is selected from the group consisting of piperidin-1-yl and 3-thiapyrrolidin-1-yl.

29. A compound selected from the group consisting of:
N-[2-diethylamino-5-{N-ethyl-N-(trifluoroacetyl)amino}pyrimidin-4-yl]-L-4'-{(pyrrolidin-1-yl)carbonyloxy}phenylalanine;
N-[2-diethylamino-5-{N-ethyl-N-(iso-propylcarbonyl)amino}pyrimidin-4-yl]-L-4'-{(pyrrolidin-1-yl)carbonyloxy}phenylalanine;
N-[2-diethylamino-5-{N-ethyl-N-(t-butylcarbonyl)amino}pyrimidin-4-yl]-L-4'-{(pyrrolidin-1-yl)carbonyloxy}phenylalanine;
N-[2-diethylamino-5-{N-ethyl-N-(furan-2-ylcarbonyl)amino}pyrimidin-4-yl]-L-4'-{(pyrrolidin-1-yl)carbonyloxy}phenylalanine;
N-[2-diethylamino-5-{N-ethyl-N-(piperidin-1-ylcarbonyl)amino}pyrimidin-4-yl]-L-4'-{(pyrrolidin-1-yl)carbonyloxy}phenylalanine;
N-[2-diethylamino-5-{N-ethyl-N-(N-ethyl-N-iso-propylaminocarbonyl)amino}pyrimidin-4-yl]-L-4'-{(pyrrolidin-1-yl)carbonyloxy}phenylalanine;
N-[2-diethylamino-5-{N-ethyl-N-(thien-3-ylcarbonyl)amino}pyrimidin-4-yl]-L-4'-{(pyrrolidin-1-yl)carbonyloxy}phenylalanine;

N-[2-diethylamino-5-{N-ethyl-N-(thien-2-ylcarbonyl) amino}pyrimidin-4-yl]-L-4'-{(pyrrolidin-1-yl) carbonyloxy}phenylalanine;

N-[2-diethylamino-5-{N-ethyl-N-(furan-3-ylcarbonyl) amino}pyrimidin-4-yl]-L-4'-{(pyrrolidin-1-yl) carbonyloxy}phenylalanine;

N-[2-diethylamino-5-{N-ethyl-N-(3-thiapyrrolidin-1-yl-carbonyl)amino}pyrimidin-4-yl]-L-4'-{(pyrrolidin-1-yl)carbonyloxy}phenylalanine;

N-[2-diethylamino-5-{N-ethyl-N-(thien-2-ylcarbonyl) amino}pyrimidin-4-yl]-L-4'-{(pyrrolidin-1-yl)carbonyloxy}-phenylalanine t-butyl ester;

N-[2-diethylamino-5-{N-ethyl-N-trifluoromethylcarbonyl)amino}pyrimidin-4-yl]-L-4'-{(pyrrolidin-1-yl)carbonyloxy}-phenylalanine t-butyl ester;

N-[2-diethylamino-5-{N-ethyl-N-t-butylcarbonyl) amino}pyrimidin-4-yl]-L-4'-{(pyrrolidin-1-yl)carbonyloxy}-phenylalanine t-butyl ester; and N-[2-diethylamino-5-{N-ethyl-N-furan-3-ylcarbonyl) amino}pyrimidin-4-yl]-L-4'-{(pyrrolidin-1-yl)carbonyloxy}-phenylalanine t-butyl ester;

or a pharmaceutically acceptable salt;

or an ester of the carboxylic acid alpha to the amino group thereof.

30. A pharmaceutical composition comprising a pharmaceutically acceptable carrier and a therapeutically effective amount of one or more of a compound according to claim 1.

* * * * *